(12) United States Patent
Tatkov

(10) Patent No.: US 11,565,067 B2
(45) Date of Patent: Jan. 31, 2023

(54) ASYMMETRICAL NASAL DELIVERY ELEMENTS AND FITTINGS FOR NASAL INTERFACES

(71) Applicant: FISHER & PAYKEL HEALTHCARE LIMITED, Auckland (NZ)

(72) Inventor: Stanislav Tatkov, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 284 days.

(21) Appl. No.: 16/798,005

(22) Filed: Feb. 21, 2020

(65) Prior Publication Data

US 2020/0282168 A1    Sep. 10, 2020

Related U.S. Application Data

(63) Continuation of application No. 14/907,510, filed as application No. PCT/NZ2014/000163 on Aug. 8, 2014, now Pat. No. 10,569,043.

(Continued)

(51) Int. Cl.
*A61M 16/06* (2006.01)
*A61M 16/10* (2006.01)
*A61M 16/00* (2006.01)

(52) U.S. Cl.
CPC .... *A61M 16/0672* (2014.02); *A61M 16/0683* (2013.01); *A61M 16/0688* (2014.02);
(Continued)

(58) Field of Classification Search
CPC ........... A61M 16/0666–0672; A61M 16/0683; A61M 16/0688; A61M 2016/0027;
(Continued)

(56) References Cited

U.S. PATENT DOCUMENTS

| 362,664 A | 5/1887 | Rothwell |
| 1,229,050 A | 6/1917 | Donald |

(Continued)

FOREIGN PATENT DOCUMENTS

| AU | 2008216375 | 8/2008 |
| AU | 2008221506 B2 | 4/2009 |

(Continued)

OTHER PUBLICATIONS

European Patent Office, Extended European Search Report, Application No. 20183115.3-1122, dated Dec. 15, 2020 in 6 pages.

(Continued)

*Primary Examiner* — Elliot S Ruddie
(74) *Attorney, Agent, or Firm* — Knobbe Martens Olson and Bear, LLP

(57) ABSTRACT

A nasal interface uses asymmetrical nasal delivery elements to deliver an asymmetrical flow through the interface to both nares or to either nare, and a mouthpiece may be inserted to maintain a leak, to improve dead space clearance in the upper airways, decrease peak expiratory pressure, reduce noise, increase safety of the therapy for smaller patients and reduce resistance in the interface allowing desired flow rates to be achieved at reduced motor speeds of associated flow generating devices. Different forms of fittings, such as sleeves or inserts can be attached to nasal delivery elements to improve or optimise the therapeutic effects of nasal high flow. It may allow high pressures to be achieved at lower flow rates, reduce noise, improve patient comfort and efficiently clear anatomical dead space.

28 Claims, 13 Drawing Sheets

Related U.S. Application Data

(60) Provisional application No. 61/870,129, filed on Aug. 26, 2013, provisional application No. 61/864,477, filed on Aug. 9, 2013.

(52) U.S. Cl.
CPC .............. *A61M 2016/003* (2013.01); *A61M 2016/0027* (2013.01); *A61M 2016/103* (2013.01); *A61M 2016/1025* (2013.01); *A61M 2202/0208* (2013.01); *A61M 2202/0225* (2013.01); *A61M 2205/42* (2013.01); *A61M 2206/20* (2013.01); *A61M 2230/205* (2013.01); *A61M 2230/432* (2013.01); *A61M 2230/435* (2013.01); *A61M 2240/00* (2013.01)

(58) Field of Classification Search
CPC .... A61M 2016/003; A61M 2016/1025; A61M 2016/103; A61M 2202/0208; A61M 2202/0225; A61M 2205/42; A61M 2206/20; A61M 2230/205; A61M 2230/432; A61M 2230/435; A61M 2240/00; A61M 15/08; A61M 15/085; A61F 5/56; A61F 5/08; A62B 23/06; Y10T 137/789
USPC ..................... 128/203.18, 203.22, 207.18
See application file for complete search history.

(56) References Cited

U.S. PATENT DOCUMENTS

| | | | |
|---|---|---|---|
| 1,248,558 | A | 12/1917 | Scribner |
| 2,168,705 | A | 8/1939 | Francisco et al. |
| 2,245,969 | A | 6/1941 | Francisco et al. |
| 2,366,067 | A | 12/1944 | Smith |
| 2,499,650 | A | 3/1950 | Kaslow |
| 2,663,297 | A | 12/1953 | Turnberg |
| 2,693,800 | A | 11/1954 | Caldwell |
| 2,735,432 | A | 2/1956 | Hudson |
| 2,868,199 | A | 1/1959 | Hudson |
| 2,902,737 | A | 9/1959 | Moran |
| 2,918,314 | A | 12/1959 | Kemintz |
| 2,962,884 | A | 12/1960 | Garrou et al. |
| 3,161,199 | A | 12/1964 | Sands |
| 3,288,136 | A | 11/1966 | Lund |
| 3,400,196 | A | 9/1968 | Le Roy |
| 3,510,155 | A | 3/1970 | Jacobus |
| 3,570,482 | A | 3/1971 | Emoto et al. |
| 3,585,692 | A | 6/1971 | Le Mire |
| 3,650,867 | A | 3/1972 | Bauer |
| 3,682,171 | A | 8/1972 | Dali et al. |
| 3,702,612 | A | 11/1972 | Schlesinger |
| 3,754,552 | A | 8/1973 | King |
| 3,799,164 | A | 3/1974 | Rollins |
| 3,858,615 | A | 1/1975 | Weigl |
| 3,877,436 | A | 4/1975 | Havstad |
| 3,972,321 | A | 8/1976 | Proctor |
| 4,000,341 | A | 12/1976 | Matson |
| 4,106,505 | A | 8/1978 | Salter et al. |
| 4,142,527 | A | 3/1979 | Garcia |
| 4,152,017 | A | 5/1979 | Abramson |
| 4,177,945 | A | 12/1979 | Schwartz et al. |
| 4,216,769 | A | 8/1980 | Grimes |
| 4,248,218 | A | 2/1981 | Fischer |
| 4,273,124 | A | 6/1981 | Zimmerman |
| 4,282,871 | A | 8/1981 | Chodorow et al. |
| 4,284,076 | A | 8/1981 | Hall |
| 4,316,458 | A | 2/1982 | Hammerton-Fraser |
| 4,328,797 | A | 5/1982 | Rollins, III et al. |
| 4,367,735 | A | 1/1983 | Dali |
| 4,422,456 | A | 12/1983 | Tiep |
| 4,441,494 | A | 4/1984 | Montalbano |
| 4,454,880 | A | 6/1984 | Muto et al. |
| 4,457,544 | A | 7/1984 | Snow et al. |
| 4,463,755 | A | 8/1984 | Suzuki |
| 4,586,273 | A | 5/1986 | Chapnick |
| 4,648,398 | A | 3/1987 | Agdanowski et al. |
| 4,648,923 | A | 3/1987 | Chapnick |
| 4,653,542 | A | 3/1987 | Tascher |
| 4,660,055 | A | 4/1987 | Payton |
| 4,676,241 | A | 6/1987 | Webb et al. |
| 4,685,456 | A | 8/1987 | Smart |
| 4,753,233 | A | 6/1988 | Grimes |
| 4,782,832 | A | 11/1988 | Trimble et al. |
| 4,808,160 | A | 2/1989 | Timmons et al. |
| 4,831,694 | A | 5/1989 | Kong |
| 4,832,010 | A | 5/1989 | Lerman |
| 4,838,258 | A | 6/1989 | Dryden et al. |
| 4,875,718 | A | 10/1989 | Marken |
| 4,913,471 | A | 4/1990 | Huneke |
| 4,915,105 | A | 4/1990 | Lee |
| 4,919,128 | A | 4/1990 | Kopala et al. |
| 4,933,231 | A | 6/1990 | Seber |
| 4,995,384 | A | 2/1991 | Keeling |
| 5,005,571 | A | 4/1991 | Dietz |
| 5,009,227 | A | 4/1991 | Nieuwstad |
| 5,025,805 | A | 6/1991 | Nutter |
| 5,042,478 | A | 8/1991 | Kopala et al. |
| 5,046,200 | A | 9/1991 | Feder |
| 5,139,476 | A | 8/1992 | Peters |
| 5,156,641 | A | 10/1992 | White |
| 5,178,163 | A | 1/1993 | Yewer, Jr. |
| 5,183,059 | A | 2/1993 | Leonardi |
| 5,222,486 | A | 6/1993 | Vaughn |
| 5,308,337 | A | 5/1994 | Bingisser |
| 5,335,656 | A | 8/1994 | Bowe et al. |
| 5,399,153 | A | 3/1995 | Caprio, Jr. et al. |
| 5,400,776 | A | 3/1995 | Bartholomew |
| 5,429,126 | A | 7/1995 | Bracken |
| 5,438,979 | A | 8/1995 | Johnson, Jr. et al. |
| 5,478,123 | A | 12/1995 | Kanao |
| 5,485,850 | A | 1/1996 | Dietz |
| 5,487,571 | A | 1/1996 | Robertson |
| 5,507,535 | A | 4/1996 | McKamey et al. |
| 5,509,409 | A | 4/1996 | Weatherholt |
| 5,513,635 | A | 5/1996 | Bedi |
| 5,533,506 | A | 7/1996 | Wood |
| 5,572,994 | A | 11/1996 | Smith |
| 5,656,023 | A | 8/1997 | Caprio, Jr. et al. |
| 5,682,881 | A | 11/1997 | Winthrop et al. |
| 5,704,916 | A | 1/1998 | Byrd |
| 5,724,677 | A | 3/1998 | Bryant et al. |
| 5,724,965 | A | 3/1998 | Handke et al. |
| 5,802,620 | A | 9/1998 | Chiang |
| 5,934,276 | A | 8/1999 | Fabro et al. |
| 6,003,213 | A | 12/1999 | Keller et al. |
| 6,017,315 | A | 1/2000 | Starr et al. |
| 6,019,101 | A | 2/2000 | Cotner et al. |
| 6,070,579 | A | 6/2000 | Bryant et al. |
| 6,109,101 | A | 8/2000 | Iwabuchi et al. |
| 6,119,693 | A | 9/2000 | Kwok et al. |
| 6,119,694 | A | 9/2000 | Correa et al. |
| 6,123,077 | A | 9/2000 | Bostock et al. |
| 6,148,929 | A | 11/2000 | Winters |
| 6,219,490 | B1 | 4/2001 | Gibertoni et al. |
| 6,270,127 | B1 | 8/2001 | Enderle |
| 6,318,364 | B1 | 11/2001 | Ford et al. |
| 6,328,038 | B1 | 12/2001 | Kessler et al. |
| 6,347,631 | B1 | 2/2002 | Hansen et al. |
| 6,367,510 | B1 | 4/2002 | Carlson |
| 6,374,826 | B1 | 4/2002 | Gunaratnam et al. |
| 6,386,198 | B1 | 5/2002 | Rugless |
| 6,415,788 | B1 | 7/2002 | Clawson et al. |
| 6,415,789 | B1 | 7/2002 | Freitas et al. |
| 6,418,928 | B1 | 7/2002 | Bordewick et al. |
| 6,418,929 | B1 | 7/2002 | Norfleet |
| 6,431,172 | B1 | 8/2002 | Bordewick et al. |
| 6,434,796 | B1 | 8/2002 | Speirs |
| 6,505,624 | B1 | 1/2003 | Campbell, Sr. |
| 6,508,249 | B2 | 1/2003 | Hoenig |
| 6,561,193 | B1 | 5/2003 | Noble |
| 6,615,830 | B1 | 9/2003 | Serowski et al. |
| 6,733,046 | B1 | 5/2004 | Rief |

(56) References Cited

U.S. PATENT DOCUMENTS

| | | |
|---|---|---|
| 6,769,431 B2 | 8/2004 | Smith et al. |
| 6,779,522 B2 | 8/2004 | Smith et al. |
| 6,796,310 B2 | 9/2004 | Bierman |
| 6,799,575 B1 | 10/2004 | Carter |
| 6,807,966 B2 | 10/2004 | Wright |
| 6,807,967 B2 | 10/2004 | Wood |
| 6,986,353 B2 | 1/2006 | Wright |
| 6,994,089 B2 | 2/2006 | Wood |
| 7,089,939 B2 | 8/2006 | Walker et al. |
| 7,140,366 B2 | 11/2006 | Smith et al. |
| 7,146,976 B2 | 12/2006 | McKown |
| 7,147,252 B2 | 12/2006 | Teuscher et al. |
| 7,152,597 B2 | 12/2006 | Bathe |
| 7,152,604 B2 | 12/2006 | Hickle et al. |
| 7,156,096 B2 | 1/2007 | Landis |
| 7,156,097 B2 | 1/2007 | Cardoso |
| 7,156,127 B2 | 1/2007 | Moulton et al. |
| 7,174,893 B2 | 2/2007 | Walker et al. |
| 7,201,169 B2 | 4/2007 | Wilkie et al. |
| 7,225,811 B2 | 6/2007 | Ruiz et al. |
| 7,296,575 B1 | 11/2007 | Radney |
| 7,318,463 B2 | 1/2008 | Tanaka et al. |
| 7,370,652 B2 | 5/2008 | Matula, Jr. et al. |
| 7,396,995 B2 | 7/2008 | Laurent et al. |
| 7,353,826 B2 | 8/2008 | Sleeper et al. |
| 7,458,615 B2 | 12/2008 | White et al. |
| 7,458,938 B2 | 12/2008 | Patel et al. |
| 7,476,212 B2 | 1/2009 | Spearman et al. |
| D586,911 S | 2/2009 | McAuley et al. |
| 7,493,902 B2 | 2/2009 | White et al. |
| 7,556,043 B2 | 7/2009 | Ho et al. |
| 7,665,465 B2 | 2/2010 | Radney |
| 7,735,490 B2 | 6/2010 | Rinaldi |
| 7,775,210 B2 | 8/2010 | Schobel et al. |
| 7,779,832 B1 | 8/2010 | Ho |
| 7,856,982 B2 | 12/2010 | Matula, Jr. et al. |
| 7,874,293 B2 | 1/2011 | Gunaratnam et al. |
| 7,900,628 B2 | 3/2011 | Matula, Jr. et al. |
| 7,942,150 B2 | 5/2011 | Guney et al. |
| RE42,843 E | 10/2011 | Srickland et al. |
| 8,028,692 B2 | 10/2011 | Ho |
| 8,042,546 B2 | 10/2011 | Gunaratnam et al. |
| 8,056,558 B2 | 11/2011 | Bracken |
| 8,136,524 B2 | 3/2012 | Ging et al. |
| 8,136,525 B2 | 3/2012 | Lubke et al. |
| 8,161,971 B2 | 4/2012 | Jaffe et al. |
| 8,171,935 B2 | 5/2012 | Cortez, Jr. et al. |
| 8,192,421 B2 | 6/2012 | Lopez et al. |
| 8,216,845 B2 | 7/2012 | Ajiro et al. |
| 8,220,463 B2 | 7/2012 | White et al. |
| 8,286,635 B2 | 10/2012 | Carroll et al. |
| 8,317,755 B2 | 11/2012 | Morrison et al. |
| 8,453,681 B2 | 6/2013 | Forrester et al. |
| D685,463 S | 7/2013 | Veliss et al. |
| 8,474,461 B2 | 7/2013 | Masella et al. |
| 8,517,022 B2 | 8/2013 | Halling et al. |
| 8,596,263 B2 | 12/2013 | Piper |
| 8,596,271 B2 | 12/2013 | Matula, Jr. et al. |
| 8,613,739 B2 | 12/2013 | Sobue |
| 8,616,203 B2 | 12/2013 | Jaffe et al. |
| 8,636,007 B2 | 1/2014 | Rummery et al. |
| 8,667,964 B2 | 3/2014 | Ho |
| 8,701,667 B1 | 4/2014 | Ho et al. |
| 8,701,668 B2 | 4/2014 | Selvarajan et al. |
| 8,757,162 B2 | 6/2014 | Veliss et al. |
| 8,789,528 B2 | 7/2014 | Carter et al. |
| D717,942 S | 11/2014 | Neff et al. |
| D724,720 S | 3/2015 | O'Connor et al. |
| 8,985,117 B2 | 3/2015 | Gunaratnam et al. |
| 8,997,747 B2 | 4/2015 | Hobson et al. |
| 9,044,562 B2 | 6/2015 | Dillingham et al. |
| 9,067,035 B2 | 6/2015 | Ophir et al. |
| 9,132,256 B2 | 9/2015 | Gunaratnam et al. |
| 9,138,554 B2 | 9/2015 | Colbaugh |
| D747,461 S | 1/2016 | Tam et al. |
| D747,794 S | 1/2016 | Greenberg et al. |
| 9,227,033 B2 | 1/2016 | Smart |
| 9,272,114 B2 | 3/2016 | Herron |
| 9,308,698 B2 | 4/2016 | Forrester et al. |
| D756,817 S | 5/2016 | Fries et al. |
| D757,250 S | 5/2016 | Veliss et al. |
| D760,379 S | 6/2016 | Smith et al. |
| 9,365,004 B2 | 6/2016 | Forrester |
| 9,393,375 B2 | 7/2016 | Hernandez et al. |
| D764,049 S | 8/2016 | Cullen et al. |
| 9,480,809 B2 | 11/2016 | Guney et al. |
| D776,252 S | 1/2017 | Hoke et al. |
| 9,539,404 B2 | 1/2017 | McAuley et al. |
| 9,550,038 B2 | 1/2017 | McAuley et al. |
| D779,432 S | 2/2017 | Wong et al. |
| 9,561,339 B2 | 2/2017 | McAuley et al. |
| 9,561,340 B2 | 2/2017 | Guney et al. |
| 9,649,463 B2 | 5/2017 | Ho et al. |
| 9,675,774 B2 | 6/2017 | Cipollone et al. |
| 9,707,010 B2 | 7/2017 | Koeth |
| 9,750,915 B2 | 9/2017 | Opperman et al. |
| 9,814,854 B2 | 11/2017 | Chua |
| 9,827,392 B2 | 11/2017 | Lei |
| 9,884,160 B2 | 2/2018 | McAuley et al. |
| 9,895,505 B2 | 2/2018 | Guney |
| 9,925,348 B2 | 3/2018 | Payton et al. |
| 9,943,660 B2 | 4/2018 | Selvarajan et al. |
| 9,962,512 B2 | 5/2018 | Cipollone et al. |
| 10,029,063 B2 | 7/2018 | Barlow |
| 10,034,995 B2 | 7/2018 | Kooij et al. |
| 10,105,099 B2 | 10/2018 | Jaffe et al. |
| 10,159,812 B2 | 12/2018 | Varga |
| 10,166,359 B2 | 1/2019 | Breckon |
| D852,053 S | 6/2019 | Kimm et al. |
| 10,350,379 B2 | 7/2019 | Sweeney et al. |
| 2001/0015204 A1 | 8/2001 | Hansen et al. |
| 2001/0029954 A1 | 10/2001 | Palmer |
| 2002/0014241 A1 | 2/2002 | Gradon et al. |
| 2002/0026934 A1 | 3/2002 | Lithgow et al. |
| 2002/0157672 A1* | 10/2002 | Gunaratnam ...... A61M 16/0638 128/205.25 |
| 2003/0116963 A1 | 6/2003 | Teuscher et al. |
| 2004/0065330 A1 | 4/2004 | Landis |
| 2004/0130150 A1 | 7/2004 | Stark |
| 2004/0216747 A1 | 11/2004 | Jones, Jr. et al. |
| 2004/0261797 A1 | 12/2004 | White et al. |
| 2005/0028822 A1 | 2/2005 | Sleeper et al. |
| 2005/0066964 A1 | 3/2005 | Bathe |
| 2005/0121038 A1 | 6/2005 | Christopher |
| 2005/0277821 A1 | 12/2005 | Payne, Jr. |
| 2006/0231100 A1 | 10/2006 | Walker et al. |
| 2007/0157932 A1 | 7/2007 | Cerbini |
| 2007/0175480 A1 | 8/2007 | Gradon et al. |
| 2007/0186931 A1 | 8/2007 | Zollinger et al. |
| 2008/0041393 A1 | 2/2008 | Bracken |
| 2008/0047560 A1 | 2/2008 | Veliss et al. |
| 2008/0092906 A1 | 4/2008 | Gunaratnam et al. |
| 2008/0223375 A1 | 9/2008 | Cortez et al. |
| 2008/0275357 A1 | 11/2008 | Cortez et al. |
| 2008/0295835 A1 | 12/2008 | Han et al. |
| 2008/0295846 A1 | 12/2008 | Han et al. |
| 2009/0000618 A1 | 1/2009 | Warren |
| 2009/0025724 A1 | 1/2009 | Herron, Jr. |
| 2009/0032018 A1 | 2/2009 | Eaton et al. |
| 2009/0032026 A1 | 2/2009 | Price et al. |
| 2009/0044808 A1* | 2/2009 | Guney ............. A61M 16/0825 128/207.18 |
| 2009/0088656 A1 | 4/2009 | Levitsky et al. |
| 2009/0133697 A1 | 5/2009 | Kwok et al. |
| 2009/0183739 A1 | 7/2009 | Wondka |
| 2009/0320851 A1 | 12/2009 | Selvarajan et al. |
| 2010/0037897 A1 | 2/2010 | Wood |
| 2010/0043801 A1 | 2/2010 | Halling et al. |
| 2010/0108073 A1 | 5/2010 | Zollinger et al. |
| 2010/0113956 A1 | 5/2010 | Curti et al. |
| 2010/0215351 A1 | 8/2010 | Forrester |
| 2010/0258132 A1 | 10/2010 | Moore |
| 2010/0258136 A1 | 10/2010 | Doherty et al. |
| 2011/0005524 A1 | 1/2011 | Veliss et al. |

(56) References Cited

U.S. PATENT DOCUMENTS

| | | |
|---|---|---|
| 2011/0067704 A1 | 3/2011 | Kooij et al. |
| 2011/0072553 A1 | 3/2011 | Ho |
| 2011/0146685 A1 | 6/2011 | Allan et al. |
| 2011/0162655 A1 | 7/2011 | Gunaratnam et al. |
| 2011/0214674 A1 | 9/2011 | Ging et al. |
| 2011/0232649 A1 | 9/2011 | Collazo et al. |
| 2011/0265796 A1 | 11/2011 | Amarasinghe et al. |
| 2011/0315148 A1 | 12/2011 | Widgerow et al. |
| 2012/0013863 A1 | 1/2012 | Sato |
| 2012/0125332 A1 | 5/2012 | Niland et al. |
| 2012/0125338 A1 | 5/2012 | Yarahmadi |
| 2012/0167894 A1 | 7/2012 | O'Leary |
| 2012/0204870 A1 | 8/2012 | McAuley et al. |
| 2012/0222678 A1 | 9/2012 | Colbaugh |
| 2012/0234319 A1 | 9/2012 | Eifler |
| 2012/0240932 A1 | 9/2012 | Gusky et al. |
| 2012/0272963 A1 | 11/2012 | Thomas et al. |
| 2012/0304999 A1 | 12/2012 | Swift et al. |
| 2012/0305001 A1 | 12/2012 | Tatkov |
| 2012/0330176 A1 | 12/2012 | Leow |
| 2013/0008447 A1 | 1/2013 | Gunaratnam et al. |
| 2013/0092165 A1 | 4/2013 | Wondka |
| 2013/0092174 A1 | 4/2013 | Jackman et al. |
| 2013/0220327 A1 | 8/2013 | Barlow et al. |
| 2013/0291870 A1 | 11/2013 | Ging et al. |
| 2013/0319421 A1 | 12/2013 | Hitchcock et al. |
| 2014/0000626 A1 | 1/2014 | O'Connor et al. |
| 2014/0053844 A1 | 2/2014 | Rummery et al. |
| 2014/0102452 A1 | 4/2014 | Forrester |
| 2014/0107517 A1 | 4/2014 | Hussain |
| 2014/0109907 A1 | 4/2014 | Doshi et al. |
| 2014/0130931 A1 | 5/2014 | Forrester |
| 2014/0166015 A1 | 6/2014 | Waggoner |
| 2014/0180157 A1 | 6/2014 | Levitsky et al. |
| 2014/0209098 A1 | 7/2014 | Dunn et al. |
| 2014/0209099 A1 | 7/2014 | Barker |
| 2014/0261433 A1 | 9/2014 | Guney |
| 2014/0261434 A1 | 9/2014 | Ng et al. |
| 2014/0276169 A1* | 9/2014 | Chua ............... A61M 16/0672 128/205.24 |
| 2014/0283827 A1 | 9/2014 | Flower et al. |
| 2014/0311494 A1 | 10/2014 | Gibson et al. |
| 2014/0326395 A1 | 11/2014 | Forrester et al. |
| 2014/0332108 A1 | 11/2014 | Forrester et al. |
| 2015/0027443 A1 | 1/2015 | Barr |
| 2015/0040898 A1 | 2/2015 | Breckon |
| 2015/0068530 A1 | 3/2015 | Apolito |
| 2015/0075530 A1 | 3/2015 | Collazo et al. |
| 2015/0083131 A1 | 3/2015 | Mals |
| 2015/0158127 A1 | 6/2015 | Lee et al. |
| 2015/0196726 A1 | 7/2015 | Skipper et al. |
| 2015/0208953 A1 | 7/2015 | Levitsky et al. |
| 2015/0276098 A1 | 10/2015 | Garrett et al. |
| 2015/0314095 A1 | 11/2015 | Himes, Jr. et al. |
| 2015/0328425 A1 | 11/2015 | Kooij et al. |
| 2015/0343165 A1 | 12/2015 | Gunartnam et al. |
| 2016/0030696 A1 | 2/2016 | Klenner et al. |
| 2016/0095997 A1 | 4/2016 | Kapust et al. |
| 2016/0144146 A1 | 5/2016 | Huddart et al. |
| 2016/0158476 A1 | 6/2016 | Tatkov |
| 2016/0199613 A1 | 7/2016 | Hadas |
| 2016/0228665 A1 | 8/2016 | Gulliver et al. |
| 2016/0235936 A1 | 8/2016 | Frater et al. |
| 2016/0271353 A1 | 9/2016 | Cheung et al. |
| 2016/0346495 A1 | 12/2016 | Payton et al. |
| 2017/0000965 A1 | 1/2017 | Corez, Jr. et al. |
| 2017/0203070 A1 | 7/2017 | Lei |
| 2017/0224944 A1 | 8/2017 | Gunaratnam et al. |
| 2017/0296767 A1 | 10/2017 | White et al. |
| 2017/0312471 A1 | 11/2017 | Anger et al. |
| 2017/0333662 A1 | 11/2017 | Ovzinsky et al. |
| 2018/0001045 A1 | 1/2018 | Cortez, Jr. et al. |
| 2018/0021535 A1 | 1/2018 | Goff et al. |
| 2018/0064899 A1 | 3/2018 | Ewers et al. |
| 2018/0078726 A1 | 3/2018 | Barraclough et al. |
| 2018/0093062 A1 | 4/2018 | Kooij et al. |
| 2018/0099110 A1 | 4/2018 | Mikhael |
| 2018/0126102 A1 | 5/2018 | Guney |
| 2018/0214653 A1 | 8/2018 | Selvarajan et al. |
| 2018/0289916 A1 | 10/2018 | Gunaratnam et al. |
| 2018/0296786 A1 | 10/2018 | Barlow |
| 2019/0275278 A1 | 9/2019 | Nakamura et al. |
| 2019/0328991 A1 | 10/2019 | Kaszas et al. |

FOREIGN PATENT DOCUMENTS

| | | |
|---|---|---|
| AU | 2011313825 | 5/2013 |
| AU | 2012397786 | 5/2015 |
| AU | 2016201534 | 3/2016 |
| AU | 2015237807 A1 | 9/2016 |
| AU | 2016222390 A1 | 9/2016 |
| AU | 2017203609 A1 | 6/2017 |
| CA | 2346628 | 11/2001 |
| DE | 472739 | 3/1929 |
| DE | 9213354 | 2/1994 |
| DE | 102006011151 | 9/2007 |
| DE | 102016014752 A1 | 6/2018 |
| EP | 229290 | 7/1987 |
| EP | 0747077 A2 | 12/1996 |
| EP | 1058570 B1 | 12/2000 |
| EP | 1078645 | 2/2001 |
| EP | 1153627 | 11/2001 |
| EP | 1621224 A2 | 2/2006 |
| EP | 1699513 A1 | 9/2006 |
| EP | 1701758 | 9/2006 |
| EP | 1342484 B1 | 6/2007 |
| EP | 1885460 | 2/2008 |
| EP | 2 022 528 | 2/2009 |
| EP | 2049054 | 4/2009 |
| EP | 2112937 | 11/2009 |
| EP | 2226341 A2 | 9/2010 |
| EP | 2292290 | 3/2011 |
| EP | 2379149 | 10/2011 |
| EP | 2438953 | 4/2012 |
| EP | 1603614 B1 | 5/2012 |
| EP | 2140902 B1 | 3/2013 |
| EP | 2624902 | 8/2013 |
| EP | 2039386 B1 | 11/2013 |
| EP | 2666795 A1 | 11/2013 |
| EP | 2717954 A1 | 4/2014 |
| EP | 2384212 B1 | 7/2014 |
| EP | 2806927 | 12/2014 |
| EP | 1646910 B1 | 8/2015 |
| EP | 2938381 | 11/2015 |
| EP | 2046430 B1 | 4/2016 |
| EP | 3030299 A1 | 6/2016 |
| EP | 3259006 A1 | 12/2017 |
| FR | 1095781 | 6/1955 |
| FR | 2558731 | 8/1985 |
| FR | 2775905 | 9/1999 |
| GB | 704819 | 3/1954 |
| GB | 1293009 | 10/1972 |
| GB | 1419841 | 12/1975 |
| GB | 2493520 A | 2/2013 |
| JP | S4815396 | 2/1973 |
| JP | 3015628 | 9/1995 |
| JP | 2002000748 | 1/2002 |
| JP | 2002052082 | 2/2002 |
| NZ | 562416 | 2/2009 |
| NZ | 571348 A | 5/2010 |
| NZ | 550348 | 2/2011 |
| NZ | 584073 A | 8/2011 |
| NZ | 586208 | 1/2012 |
| NZ | 591310 | 7/2012 |
| NZ | 594204 A | 12/2012 |
| NZ | 595424 | 12/2012 |
| NZ | 587745 | 1/2013 |
| NZ | 603994 | 6/2014 |
| NZ | 605600 | 11/2014 |
| NZ | 615814 | 5/2015 |
| NZ | 623720 | 10/2015 |
| NZ | 623338 | 12/2015 |
| NZ | 626589 | 1/2016 |
| NZ | 630742 | 2/2016 |

(56) References Cited

FOREIGN PATENT DOCUMENTS

| | | |
|---|---|---|
| NZ | 709716 | 2/2016 |
| NZ | 630741 | 3/2016 |
| NZ | 706053 | 10/2016 |
| NZ | 714595 | 6/2017 |
| NZ | 715073 | 6/2017 |
| NZ | 713510 | 10/2017 |
| NZ | 733922 | 10/2017 |
| NZ | 720223 | 12/2017 |
| NZ | 722816 | 2/2018 |
| NZ | 725632 | 5/2018 |
| WO | WO81/03282 | 11/1981 |
| WO | WO89/09043 | 10/1989 |
| WO | WO1997/012570 | 4/1997 |
| WO | WO97/17034 | 5/1997 |
| WO | WO1998036687 A1 | 8/1998 |
| WO | WO98/44973 | 10/1998 |
| WO | WO0059567 | 10/2000 |
| WO | WO0132250 | 5/2001 |
| WO | WO0197892 | 12/2001 |
| WO | WO2002005883 | 1/2002 |
| WO | WO03006095 | 1/2003 |
| WO | WO03/066145 | 8/2003 |
| WO | WO 03/068301 | 8/2003 |
| WO | WO2003/090827 | 11/2003 |
| WO | WO2004030736 | 4/2004 |
| WO | WO2005/063327 | 9/2004 |
| WO | WO2004073778 | 9/2004 |
| WO | WO2005079726 | 9/2005 |
| WO | WO2005070063 A3 | 11/2005 |
| WO | WO2006120683 A9 | 5/2007 |
| WO | WO2008/007985 | 1/2008 |
| WO | WO2009099995 | 8/2009 |
| WO | WO2009109005 | 9/2009 |
| WO | WO2010084183 | 7/2010 |
| WO | WO2011059346 | 5/2011 |
| WO | WO2011061648 | 5/2011 |
| WO | WO2011062510 | 5/2011 |
| WO | WO2011/121466 | 10/2011 |
| WO | WO2011141841 | 11/2011 |
| WO | WO2013042004 | 3/2013 |
| WO | WO2013/112545 | 8/2013 |
| WO | WO2013/138732 | 9/2013 |
| WO | WO2013/157960 | 10/2013 |
| WO | WO 2013/157960 A1 | 10/2013 |
| WO | WO2014015382 | 1/2014 |
| WO | WO2014092703 | 6/2014 |
| WO | WO2014/142681 | 9/2014 |
| WO | WO2015009172 | 1/2015 |
| WO | WO2015/013761 | 2/2015 |
| WO | WO2015/020540 | 2/2015 |
| WO | WO 2015/145390 | 10/2015 |
| WO | WO2015151019 | 10/2015 |
| WO | WO2015156690 A1 | 10/2015 |
| WO | WO2015164921 | 11/2015 |
| WO | WO2015192186 A1 | 12/2015 |
| WO | WO2015193833 | 12/2015 |
| WO | WO2016048172 | 3/2016 |
| WO | WO2016122716 A1 | 8/2016 |
| WO | WO2016133781 | 8/2016 |
| WO | WO2016157103 A1 | 10/2016 |
| WO | WO2016157105 A1 | 10/2016 |
| WO | WO2016159787 A1 | 10/2016 |
| WO | WO2017004404 A1 | 1/2017 |
| WO | WO2017059494 | 4/2017 |
| WO | WO2017160166 | 9/2017 |
| WO | WO2017216650 | 12/2017 |
| WO | WO2018005851 A1 | 1/2018 |
| WO | WO2018108670 A1 | 6/2018 |

OTHER PUBLICATIONS

PCT International Search Report and Written Opinion; PCT/NZ2014/000163; 13 pages; dated Nov. 10, 2014.

Examination Report, European Patent Office, Application No. 14 833 902.1-1122, dated Mar. 6, 2019, in 3 pages.

\* cited by examiner

ASYMMETRICAL NASAL DELIVERY ELEMENTS AND FITTINGS FOR NASAL INTERFACES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Technical Field of the Invention

The present invention generally relates to a nasal interface. More particularly, the present invention relates to asymmetrical nasal delivery elements for a nasal interface and other arrangements for achieving asymmetric flow or partial unidirectional flow.

Description of the Related Art

Humidifiers are used to provide humidified respiratory gases to a patient. Gases are delivered to the patient via a patient interface. Examples of a patient interface include an oral mask, a nasal mask, a nasal cannula, a combination of oral and nasal mask, and the like.

Nasal interfaces can be used to deliver a high flow of gases to a patient. Nasal delivery elements are inserted into the nose of a patient to deliver the required therapy. The nasal delivery elements may be required to seal or semi-seal at the nose, or may not be required to seal at the nose, to deliver the therapy. Nasal high flow typically is a non-sealing therapy that delivers relatively high-volume flow to the patient through a nasal interface, which flow may be sufficient to meet or exceed the patient's inspiratory flow rate.

SUMMARY OF THE INVENTION

Although prongs for nasal interfaces exist in the prior art, an aspect of at least one of the embodiments disclosed herein includes the realization that there are problems with the insertion of these prior art prongs into the nose of a patient. Prongs in the art require high motor speeds of the flow generating device to deliver the desired flow rate to the patient. A flow generating device is a device that delivers a flow of gas to a patient.

If the interface is suddenly occluded, the static pressure may increase to equal the backpressure in the system, which may potentially reach undesirable levels. The undesirably high static pressure is intensified for child and infant prongs because the reduced prong diameter required to fit the nares of a child or infant can increase resistance to flow through the interface to the patient.

Currently there are few different sized nasal delivery elements available to better fit a patient, and it can be difficult to optimise dead space clearance and delivered pressure to the patient. The current options may use supplemental oxygen, require more heating, more water and may not provide a high level of patient comfort. Undesirably high flows or excessively high flows are being provided to patients to achieve the desired pressure effects with the existing interfaces. A nasal delivery element of a nasal interface with a smaller diameter may have a high leak and as a result will deliver lower pressure to a patient. A large diameter may not be as efficient at clearing anatomical dead space from the patient airways.

A system is disclosed that uses nasal high flow in combination with asymmetrical nasal delivery elements for a nasal interface to deliver respiratory gases to a patient via an asymmetrical flow. Asymmetrical nasal delivery elements can provide the patient with increased dead space clearance in the upper airways, Due to a decrease in peak expiratory pressure, noise can be reduced, and asymmetrical nasal delivery elements may provide a more desirable therapy for infant use due to mitigation of the risk of completely sealing the airways of the patient. The asymmetry of the nasal delivery elements can reduce the resistance to flow through the interface, which can achieve desired flow rates using lower backpressure and/or lower motor speeds of the flow generating device.

Different embodiments disclose a system that modifies the pressure effects during nasal high flow while maintaining efficient dead space clearance, by adding fittings such as but not limited to, sleeves or inserts to the nasal interface. It may increase pressure swings generated during breathing, increase jetting effects, improve patient comfort, more efficiently clear dead space and increase expiratory pressure. The use of fittings may reduce the required operational flow, which may result in less noise, reductions in heating, oxygen and water usage, desirable or optimised therapeutic effects of nasal high flow. Thus a lower flow rate may be able to achieve a higher pressure.

Accordingly, in one aspect the present invention relates to a nasal interface comprising asymmetrical nasal delivery elements, the asymmetrical nasal delivery elements comprising a first nasal delivery element that is a prong and a second nasal delivery element that is a prong or a pillow, the prong or pillow of the second nasal delivery element having a greater internal cross-sectional area on a plane perpendicular to the airflow direction than a prong of the first nasal delivery element, which causes asymmetrical flow or partial unidirectional flow of gases at the nares of a subject, to improve dead space clearance, preferably to reduce the volume of anatomical dead space within the volume of the airway of a subject, to reduce peak expiratory pressure, to reduce noise, and/or to reduce resistance to flow at the patient interface.

In various embodiments the first and second nasal delivery elements may comprise
 (1) an orifice without a nasal prong adapted in use to rest adjacent one nare and a nasal prong or a nasal pillow adapted in use to engage the other nare, or
 (2) a first nasal prong having a first cross-sectional area and a second nasal prong or a nasal pillow having a second cross-sectional area, the second cross-sectional area being greater than the first cross-sectional area, or
 (3) a first nasal prong having a first outer circumference and a second nasal prong or a nasal pillow having a second outer circumference, the second outer circumference being greater than the first outer circumference, or
 (4) a first nasal prong having a first cross-sectional area and a first outer circumference and a second nasal prong or a nasal pillow having a second cross-sectional area and a second outer circumference, the second cross-sectional area and second outer circumference being greater than the first cross-sectional area and first outer circumference.

In various embodiments the second cross-sectional area may be about 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42.5, 43, 43.5, 44, 44.5, 45, 45.5, 46, 46.5, 47, 47.5, 48, 48.5, 49, 49.5, or 50 mm², and useful ranges may be selected between any of these values (for example, about 1.5 to about 10, about 1.5 to about 20, about 1.5 to about 30, about 1.5 to about 40, and about 1.5 to about 50 mm²).

In various embodiments the first cross-sectional area may be about 20, 21, 22, 23, 24, 25, 26, 27, 28, 29, 30, 311 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, or of the second cross-sectional area, and useful ranges may be selected between any of these values (for example, about 20 to about 30, about 20 to about 40, about 20 to about 50, about 20 to about 60, about 20 to about 70, and about 20 to about 80%).

In various embodiments the second cross-sectional area may be about 1.5 to about 50 mm² and the first cross-sectional area may be about 20% to about 80% of the second cross-sectional area, preferably about 50%.

In various embodiments the ratio of the first cross-sectional area to the second cross-sectional area may be at least about 1:1.2, 1:1.25, 1:1.3, 1:1.35, 1:1.4, 1:1.451, 1:1.551, 1:1.6, 1:1165, 1:1.71, 1:1.75, 1:1.8, 1:1.85, 1:1.9, 1:1.95, 1:2, 1:2.05, 1:2.1, 1:2.151 1:2.21 1:2.251 1:2.31 1:2.351 1:2145, or 1:215, and useful ranges may be selected between any of these values (for example, about 1:1.2 to about 1:2.5). Preferably the ratio may be about 1:2.

In various embodiments the second outer circumference may be about 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, or 30 mm, and useful ranges may be selected between any of these values (for example, about 7.5 to about 10, about 7.5 to about 15, about 7.5 to about 20, about 7.5 to about 25, and about 7.5 to about 30 mm).

In various embodiments the first outer circumference may be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 501 51, 52, 53, 54, 55, 56, 57, 58, 59, 60, 61, 62, 63, 641 65, 66, 67, 68, 69, 70, 71, 72, 73, 74, 75, 76, 78, 79, or 80% of second outer circumference, and useful ranges may be selected between any of these values (for example, about 20 to about 30, about 20 to about 40, about 20 to about 50/about 20 to about 60, about 20 to about 70, and about 20 to about 80%).

In various embodiments the second outer circumference may be about 7.5 mm to about 30 mm and the first outer circumference may be about 20% to about 80% of the second outer circumference, preferably about 50%.

In various embodiments the ratio of the first outer circumference to the second outer circumference may be at least about 1:1.2, 1:1.25, 1:1.3, 1:1.35, 1:1.4, 1:1.45, 1:1.55, 1:1.65, 1:1.7, 1:1.75, 1:1.8, 1:1.9, 1:1.95, 1:2, 1:2.05, 1:2.1, 1:2.15, 1:2.2, 1:2.25, 1:2.3, 1:2.35, 1:2.45, or 1:2.5, and useful ranges may be selected between any of these values (for example, about 1:1.2 to about 1:2.5). Preferably the ratio may be about 1:2.

In various embodiments, the nasal interface may be adapted so that fittings may be attached to the nasal delivery elements of the interface to alter the shape or inner or outer diameters of the nasal delivery elements to efficiently clear dead space, reduce operational flow, and reduce noise.

In various embodiments, one nasal delivery element may comprise a single lumen, or both nasal delivery elements may comprise a single lumen.

In another aspect the present invention relates to user interface assembly comprising a nasal interface as described herein, a securement system for the user interface and/or a component associated with the user interface (e.g. such as a tube or tubing), and/or a tube connected to the user interface providing at least a part of a breathing circuit for a user of the interface.

In various embodiments the securement system may comprise a two-part releasable attachment (or connection) arrangement, the arrangement comprising a dermal patch and a user interface patch, (1) the dermal patch having a patient side and an interface side,
   (a) the patient side of the dermal patch being attachable to the skin of a user, (e.g. by an adhesive, generally being of a dermatologically sensitive adhesive such as a hydrocolloid),
   (b) the interface side of the dermal patch being provided with the first part of a two-part releasable attachment or connection system, and
(2) the user interface patch having an interface side and patient side,
   (a) the patient side of the user interface patch being provided with the complimentary second part of the two-part releasable attachment or connection system,
   (b) the interface side of the user interface patch being attachable (or connectable) to the user interface and/or the component associated with the user interface (e.g. a tube or tubing).

In various embodiments the tube comprises
(1) a tubular body, the body defining a lumen extending between open terminal ends of the body,
(2) an internal form enclosed within the lumen and supportive of the tubular body, and
(3) a coating encapsulating the internal form, the coating securing the internal form to the tubular body.

In various embodiments the interface comprises
(1) at least one nasal prong, the prong having a gas outlet adapted to be inserted into a user's nare and a gas inlet fluidly connected to the gas outlet,
(2) the at least one nasal prong comprising a backing, the backing configured to rest on a user's face, wherein a lip extends about at least a part of the perimeter of a rear surface of the backing, the rear surface configured for receiving or retaining the user interface patch, such that in use, the user interface patch may be releasably attachable or connectable to, or with, the dermal patch affixed to a user's face.

In various embodiments the lip is a barrier.

In various embodiments the lip extends at least about the perimeter of a region substantially adjacent to a prong associated with the backing.

In various embodiments the lip is an endless lip extending about the perimeter of the rear surface of the backing.

In various embodiments the lip is a series of one or more separate lips.

In various embodiments the one or more separate lips are adjacent or adjoining or overlapping lip portions.

In various embodiments, in use, the lip substantially forms a fluid (e.g. liquid) seal, or barrier to fluid, between the rear surface of the backing and a cannula facing surface of the user interface patch.

In various embodiments the backing is substantially planar or flat or contoured (such as a pre-formed curve) backing configured to rest on a user's face.

In various embodiments the backing assists as a stabilizer of the prong(s) in the nare(s) of a user.

In various embodiments the at least one backing extends laterally outward from the at least one nasal prong, away from the septum of a user.

In various embodiments the lip(s) is hydrophobic.

In various embodiments the lip(s) comprises at least one outer perimeter lip portion and at least one inner perimeter lip portion, each of said lips provided for contacting with a user's face.

In various embodiments the nasal interface may further comprise
(1) a face mount part comprising a base portion and the nasal delivery elements, and
(2) a gases flow manifold part having a gases inlet for receiving a flow of gas from a gas source, and a gases outlet for delivering the flow of gas to the nasal delivery elements of the face mount part, the manifold part being adapted to be received by the base portion of the face mount part to fluidly connect the outlet of the manifold with the nasal delivery elements of the face mount part, and wherein the manifold part further comprises a groove at the outlet to establish a gap between the base portion of the face mount part and the manifold part in a region of the base portion configured to locate adjacent a user's philtrum in use to thereby eliminate or at least alleviate pressure on the user's septum from the manifold part in use.

In various embodiments the face mount part may comprise at least one substantially horizontal side entry passage to the interior of the base portion for releasably receiving the outlet of the manifold part therethrough.

In various embodiments the face mount part may comprise a pair of opposed side entry passages to the interior of the base portion, each adapted to releasably receive the outlet of the manifold part therethrough.

In various embodiments the gases flow manifold part may be formed from a relatively harder material than the face mount part.

In various embodiments the gases flow manifold part may be formed from a substantially rigid plastics material, such as polycarbonate.

In various embodiments the face mount part may be formed from a substantially soft plastics material, such as silicone.

In various embodiments the nasal interface may further comprise headgear comprising a strap forming a part of the headgear for assisting in retaining or stabilising of the nasal interface upon a user, wherein the strap, or a section of the strap, to be located upon or to be placed in contact with the face or a portion of a user's face includes a surface region for frictionally engaging with the user's face, the surface region being of a relatively higher frictional surface material than the remainder of the strap forming the or a part of the headgear.

In various embodiments the strap or a respective section of the strap, includes two symmetric surface regions for frictionally engaging with two symmetric portions on either side of the user's face.

In various embodiments a remainder of the strap is arranged to extend as a non-facial contacting strap or section of strap which is to extend beyond the user's face or the portion of the user's face.

In various embodiments, each surface region for frictionally engaging with the user's face or a portion of the user's face including the relatively higher frictional surface material assists with retaining or stabilising of a patient interface upon the face of a user.

In various embodiments each surface region comprises a material applied to the strap or the respective section of strap.

In various embodiments the material applied is in the form of a sleeve positioned about the strap or the respective section of strap.

In various embodiments the sleeve is configured to removeably couple about the strap or the section of the strap.

In various embodiments the strap or the respective section of the strap extends through a passage in the sleeve.

In various embodiments the strap or the respective section of the strap is adapted to be threaded through the passage.

In various embodiments the material applied is in the form of a material coated upon the strap or the respective section of strap.

In various embodiments the material applied is overmoulded upon the strap or the respective section of strap.

In various embodiments the material applied is smooth and comfortable for skin contact.

In various embodiments the material applied is a thermoplastic elastomer.

In various embodiments each surface region is a surface of wider surface area at an end to be located more adjacent to the patient interface than the surface area of an opposing end more distant from the patient interface.

In various embodiments each surface region tapers from the relatively wider surface area to the relatively lesser surface area.

In various embodiments the strap or each section of the strap including the surface region further comprises a component of the strap configured to releasably couple the patient interface.

In various embodiments each portion of the user's face includes a cheek of the user.

In another aspect the present invention relates to a method of delivering gas to the airway of a subject in need thereof, improving the ventilation of a subject in need thereof, reducing the volume of anatomical dead space within the volume of the airway of a subject in need thereof, and/or treating a respiratory condition in a subject in need thereof, the method comprising delivering a continuous flow of gas to the nares of a subject through a nasal interface comprising asymmetrical nasal delivery elements to generate an asymmetrical flow or a partial unidirectional flow of gases at the nares.

In various embodiments the method may comprise improving the ventilation of a subject in need thereof includes reducing peak expiratory pressure, reducing noise during expiration, and/or reducing resistance to flow at the patient interface.

In various embodiments the gas may be delivered to one nare of the subject at a first flow rate of about 5, 10, 15, 20, 25, 30, 35, 40, 45, 50, 55, or 60 L/min, and useful ranges may be selected between any of these values (for example, about 5 to about 10, about 5 to about 20, about 5 to about 30, about 5 to about 40, about 5 to about 50, and about 5 to about 60 L/min).

In various embodiments the flow rate to the other nare of the subject may be at a second flow rate that may be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, or 80% of the first flow rate, and useful ranges may be selected between any of these values (for example, about 20 to about 30, about 20 to about 40, about 20 to about 50, about 20 to about 60, about 20 to about 70, and about 20 to about 80%).

In various embodiments the gas may be delivered to one nare of the subject at a first flow rate of about 5 L/min to about 60 L/min and to the other nare of the subject at a second flow rate that may be about 20% to about 80% of the first flow rate, preferably about 50%.

In various embodiments the subject's mouth may be closed or sealed.

In various embodiments the subject's mouth may be open.

In various embodiments the method may further comprise inserting a mouthpiece into the mouth of the subject, to maintain a leak from the mouth of the subject into the atmosphere, a negative pressure line, or an expiratory limb, or to increase or control dead space clearance.

In various embodiments sound generated by the expiration of gas through the nares' may be less than the sound generated by nasal expiration during nasal high flow therapy conducted at an equivalent flow rate using a nasal interface that comprises symmetrical nasal delivery elements.

In various embodiments the gas pressure in the subject's airway may be estimated and/or measured.

In various embodiments the average gas pressure in the subject's airway may be maintained at a level of less than about 4 cm $H_2O$, preferably at a level of less than about 3.5, 3, 2.5, 5 or 1 cm $H_2O$, preferably with the subject's mouth open or closed, preferably with the subject's mouth closed.

In various embodiments the oxygen concentration of the subject's airway may be measured.

In various embodiments the oxygen concentration of the subject's airway may be maintained at a substantially constant level or increased.

In various embodiments the carbon dioxide concentration of the subject's airway may be measured.

In various embodiments the carbon dioxide concentration of the subject's airway may be maintained at a substantially constant level or reduced.

In various embodiments the molar fraction of carbon dioxide in the upper airway of the subject may be reduced, preferably by at least about 1, 2, 3, 4, 5, 6, 7, 8, 9, or 10 molar % or more, compared to the molar fraction of carbon dioxide in the upper airway of the subject when breathing without assistance.

In various embodiments the molar fraction of carbon dioxide in the upper airway of the subject may be reduced, preferably by at least about 1, 2, 3, 4, 5, 6, 7, 8, 9, or 10 molar % or more, compared to nasal high flow therapy conducted at an equivalent flow rate using a nasal interface that comprises symmetrical nasal delivery elements.

In various embodiments the peripheral capillary oxygen saturation of the subject may be measured.

In various embodiments the peripheral capillary oxygen saturation of the subject may be maintained at a substantially constant level or increased.

In various embodiments herein the peripheral capillary oxygen saturation of the subject may be increased compared to nasal high flow therapy conducted at an equivalent flow rate using a nasal interface that comprises symmetrical nasal delivery elements.

In various embodiments the subject may be hypoxic or hypoxemic before the method is carried out.

In various embodiments the respiratory condition may be chronic obstructive pulmonary disease, asthma, pneumonia, bronchitis, or emphysema.

In various embodiments the gas may be delivered to the airway of the subject for at least about 15, 20, 25, 30, 35, 40, 45, 50, 55, 60, 90, 120, 150, or 180 minutes or more, or for at least about 1, 2, 3, 6, 9, 12, 15, 18, 21, 24, 36, 48, 60, or 72 hours or more, or for at least about 1, 2, 3, 4, 5, 6, or 7 days or more, and useful ranges may be selected between any of these values (for example, about 15 minutes to about 7 days, about 15 minutes to about 72 hours, about 15 minutes to about 180 minutes, about 30 minutes to about 7 days, about 30 minutes to about 72 hours, and about 30 minutes to about 180 minutes).

In various embodiments the method may be carried out using an interface of the invention.

BRIEF DESCRIPTION OF THE DRAWINGS

These and other features, aspects, and advantages of the present invention will be described with respect to the following figures, which are intended to illustrate and not to limit the preferred embodiments.

FIGS. 9A-9l are different embodiments of an asymmetrical nasal interface, with one nasal delivery element having a greater internal cross-sectional area on a plane perpendicular to the airflow direction than the other nasal delivery element.

DETAILED DESCRIPTION OF THE PREFERRED EMBODIMENT

Figure 1:
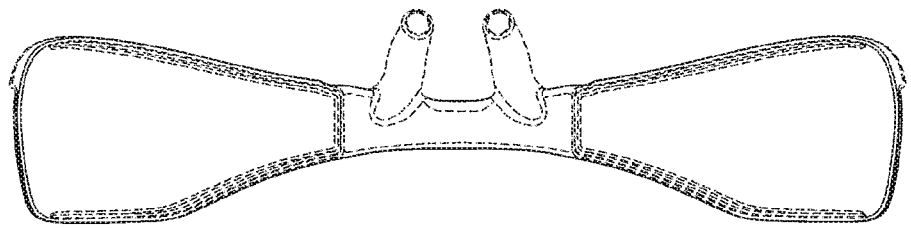
FIG. 1 is a nasal interface as known in the prior art.

Nasal interfaces (FIG. 1) can be used to deliver a high flow of gases to a patient. Nasal delivery elements, such as prongs or nasal pillows, are inserted into the nose of a patient to deliver the required therapy. The nasal delivery elements may be desired to seal or semi-seal at the nose, or may not be required to seal at the nose, to deliver the therapy. As used herein, prongs typically refer to nasal delivery elements designed to not seal or to only semi-seal at the nose, while nasal pillows typically refer to nasal delivery elements designed to seal at the nose. Nasal high flow (NHF) typically is a non-sealing therapy that delivers relatively high-volume flow to the patient through a patient interface, such as a nasal interface. A nasal interface as herein described may refer to, but is not limited to, a nasal cannula.

Figure 2:
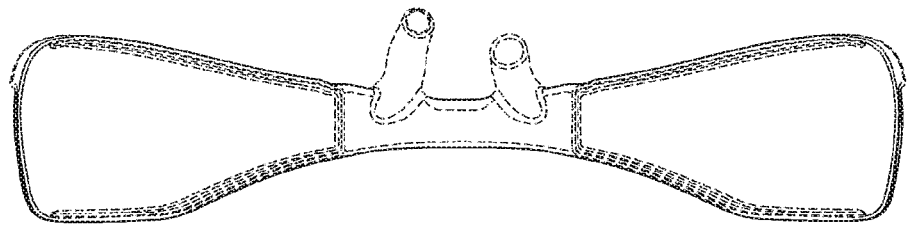
FIG. 2 is a nasal interface with asymmetrical nasal delivery elements.

Disclosed is a system to deliver gases to a patient through an asymmetrical cannula interface (FIG. 2). An asymmetrical interface or asymmetrical nasal delivery elements, as described herein, refers to a interface where the nasal delivery elements differ in length (including the substantial or complete absence of a nasal delivery element), internal or external diameter, angle or form, or any combination of these. The system allows an asymmetrical flow to be delivered through the interface to both nares or to either nare. Asymmetrical flow as described herein refers to a flow that differs within the interface or within the nose. In this way, a different flow may be delivered by each nasal delivery element, or the flow may differ between inspiration and expiration, or the delivered flow may be a combination of the above. An asymmetrical flow may also include partial unidirectional flow. Delivery of asymmetrical flow may improve clearance of dead space in the upper airways, decrease peak expiratory pressure, increase safety of the therapy particularly for children and infants, and reduce resistance to flow in the interface. An asymmetrical interface, nasal delivery elements or interface as described herein includes interfaces or systems configured to produce such asymmetrical flow through asymmetrical nasal delivery elements or otherwise.

Pressure generated by NHF depends on flow through the cannula interface, the size of the nasal delivery elements and/or nares of the patient, and the breathing cycle. If flow, leak, or a combination of flow and leak, is asymmetrical through the interface, the flow through the nose may become asymmetrical during breathing. Partial or total unidirectional flow may occur and there may be improved clearance of anatomical dead space as the air is continuously flushed from the upper airways. Total unidirectional flow may be discomforting to a subject. Partial unidirectional flow may be preferred whereby less discomfort is experienced by a subject. Total unidirectional flow as described herein occurs if flow enters one nare by a nasal delivery element and exits via the other nare via a nasal delivery element, vents to the atmosphere, due to the absence of a nasal delivery element, or the like. Partial unidirectional flow as described herein refers to flow that may enter the nose via both nares and leave the nose from one nare, flow that may enter the nose through one nare and leave the nose via both nares, or different proportions of flow that may enter the nose through both nares and different proportions of flow that may leave the nose through both nares, and is preferably flow that may enter the nose via both nares and leave the nose from one or both nares.

NHF delivered through an asymmetrical cannula interface can involve making an interface in which the nasal delivery elements are of different length, internal or external diameter, or a combination of these (FIG. 2). Particularly for children or infants, nasal delivery elements will have a small internal diameter and thus higher resistance to gas flow. By using nasal delivery elements that are different lengths, each nasal delivery element may have a different internal diameter (e.g., minimum internal diameter or area). A longer nasal delivery element may have a smaller internal diameter and higher resistance to gas flow; a shorter nasal delivery element may have a larger internal diameter (e.g., larger minimum internal diameter), hence lower resistance to gas flow at the interface. A decreased resistance to flow allows the desired flow to be achieved using lower backpressure, or a lower motor speed of the gas generating device, or a combination of the two.

Asymmetrical nasal delivery elements may cause the peak expiratory pressure to decrease due to the different lengths of the nasal delivery elements at the nose which may provide different internal diameters for each nasal delivery element. During exhalation a patient may be breathing against less pressure in the system as one nare may be open to the atmosphere, or a nasal delivery element may have a greater internal diameter compared to the other nasal delivery element or otherwise have less resistance to exhalation flow compared to the other nasal delivery element, which may reduce the pressure required to exhale.

Figure 3:
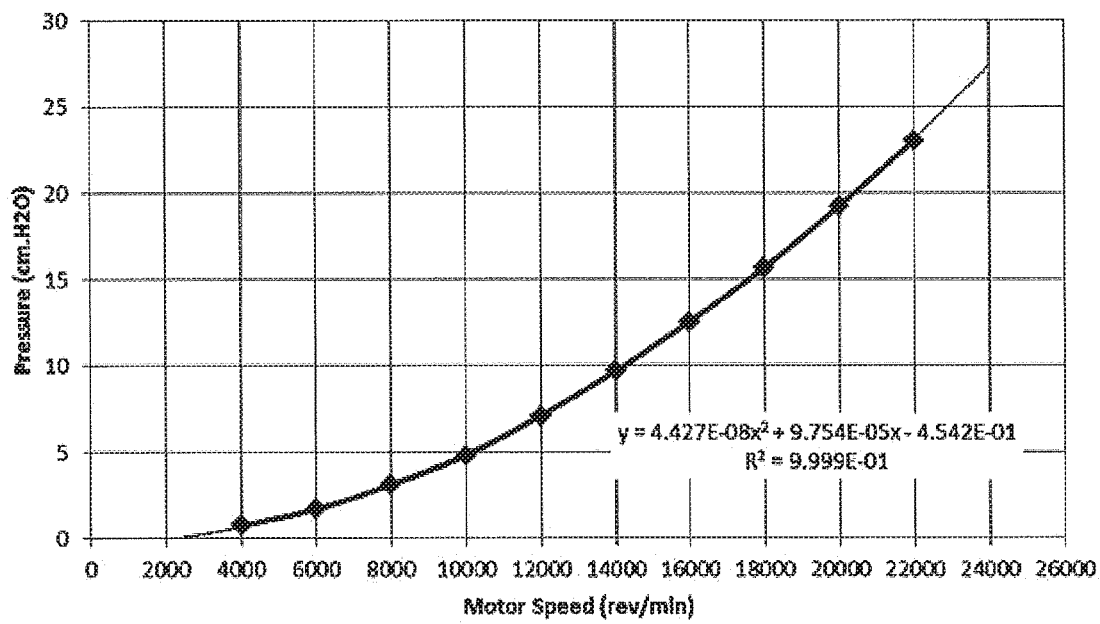
FIG. 3 is a graphical depiction of pressure and motor speed.

In an example, an asymmetrical nasal interface used with (e.g., coupled via a conduit or breathing tube) a gas generating device, such as an AIRVO™ flow generator from Fisher & Paykel Healthcare Ltd., decreases the resistance to flow. This may cause the motor speed of the AIRVO™ to drop from a range of 18,000-22,000 RPM to a range of 14,000-18,000 RPM while continuing to achieve a suitable flow for the desired therapy (e.g., NHF), such as about 8 L/min. FIG. 3 illustrates a relationship between the motor speed of the AIRVO™ flow generator and the generated backpressure in the system. The asymmetrical nasal delivery elements may cause a reduction of the backpressure generated in the system. As a result, if an interface is suddenly jammed into the nose, the maximum pressure generated will not exceed the backpressure in the system, which may improve the safety of the system during delivery of NHF.

For a smaller patient, as in an infant or a child, use of asymmetrical nasal delivery elements may reduce over-insertion of both prongs into the nares, when the nares are too small with respect to the prongs, which could result in an undesired semi-seal or seal. Asymmetrical flow may be delivered to the patient even if only one prong is positioned tightly in the nose. The asymmetrical interface improves the performance of the therapy for infants as compressed gas may be used in a system without pressure control.

Figure 4A:
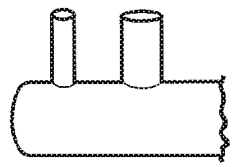
FIGS. 4a-4n are different embodiments of a nasal interface with asymmetrical nasal delivery elements.
Figure 4B:
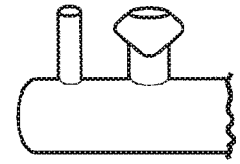
Figure 4C:
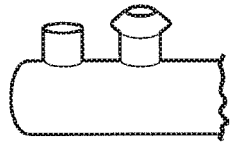
Figure 4D:
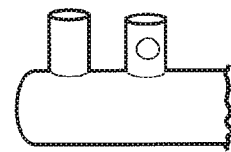
Figure 4E:
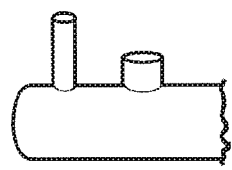
Figure 4F:
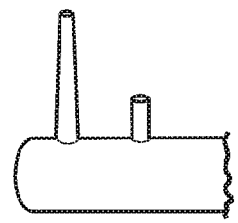
Figure 4G:
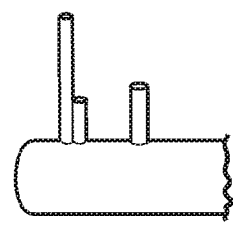
Figure 4H:
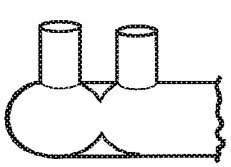
Figure 4I:
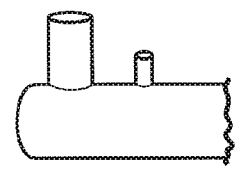
Figure 4J:
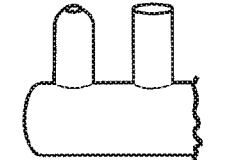
Figure 4K:
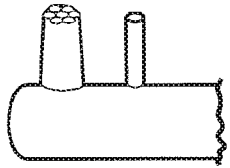
Figure 4L:
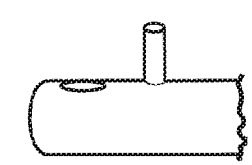
Figure 4M:
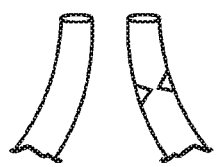
Figure 4N:
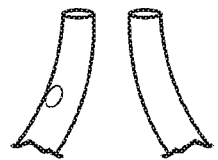

FIGS. 4a-4n show other embodiments that include but are not limited to: nasal delivery elements with the same internal or external diameter or nasal delivery elements with a different internal or external diameter (FIGS. 4a and 4i). The nasal delivery elements may have a different form, either different from that described above, or from each other (e.g., one prong and one nasal pillow). At least one nasal delivery element may be sealed (FIGS. 4b and 4c). At least one nasal delivery element may have at least one ventilation hole. The nasal delivery elements may be symmetrical with one or more ventilation holes in at least one nasal delivery element producing asymmetrical flow during breathing (FIGS. 4d and 4n). At least one nasal delivery element may have a narrowing at the tip, which may produce asymmetrical flow through the nasal delivery elements in a low impedance gas delivery system as a result of a pressure difference in the nose during breathing (FIG. 4j). The narrowest point may be proximal to the flow source, thus the breathing cycle may not affect flow through the asymmetrical nasal delivery elements. The interface may be designed in a way that the left and right nasal delivery elements can be swapped. The interface may have an option to divert flow through either the symmetrical or asymmetrical nasal delivery elements, to an individual nasal delivery element, by varying the resistance within the interface (FIGS. 4h and 4m), or by partial over-insertion of the into nose. The nasal delivery elements may have different lengths (FIGS. 4e and 4i), or at least one nasal delivery element may extend into the nose to the nasal valves (FIG. 4f). More than two nasal delivery elements may be used with varying internal or external diameter or with different lengths, or a combination of these (FIGS. 4g and 4k).

Figure 6A:
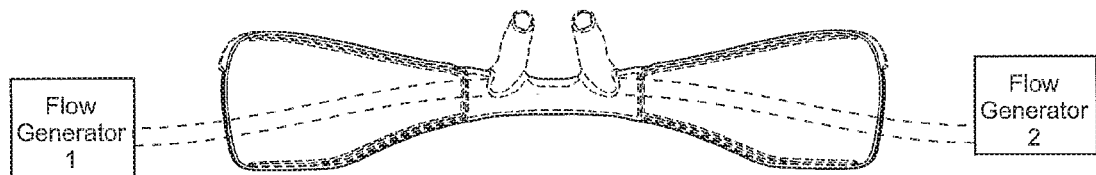
FIGS. 6a-6c are different embodiments of a nasal interface with different flow supplies.
Figure 6B:
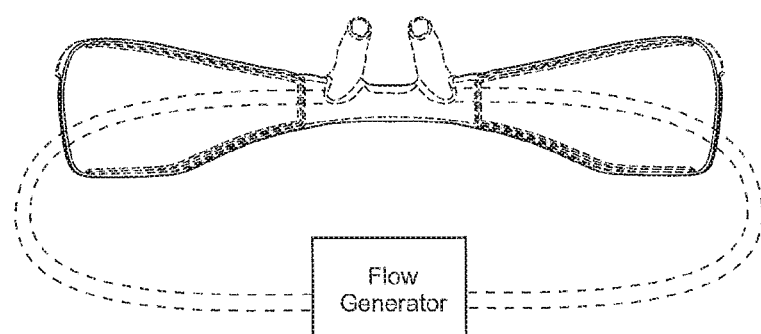
Figure 6C:
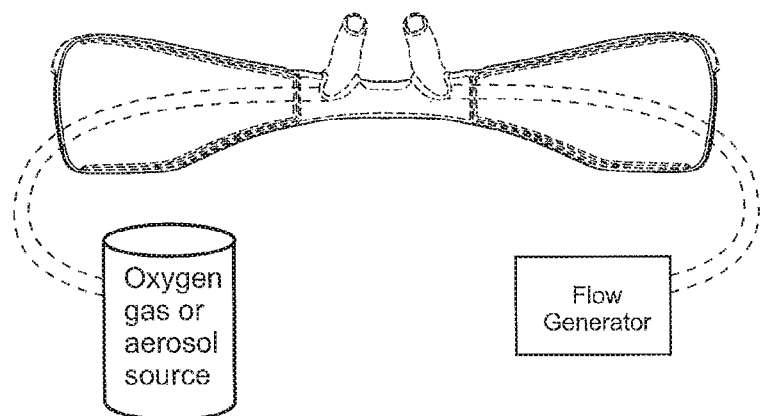

Pressure and flow may be measured and controlled in the nares simultaneously or separately. Flow may be continuous in one nare, while it is varied in the other nare according to the breathing cycle. Different interfaces, each delivering asymmetrical flow in the nose, may be used to continuously deliver supplemental oxygen, and to deliver continuous or variable nasal high flow. One nasal delivery element may be used to deliver oxygen, gases, aerosols or the like to the patient while another nasal delivery element may be used to deliver a higher flow of air, or a different flow of oxygen, gases, aerosols or the like to the patient. Each nasal delivery element may supply different flow rates to the patient, and may connect to different flow generating elements (FIGS. 6a-6c).

The system may improve the performance of NHF therapy, particularly in the therapy delivered to infants and children. It may reduce resistance compared to existing nasal interfaces and may extend and improve functionality of respiratory devices without modification of the hardware or software.

Asymmetrical flow useful herein can be provided by a nasal interface using any form of pressure support, such as continuous positive airway pressure (CPAP) or non-invasive therapy (NIV). Anatomical dead space can be cleared by transnasal unidirectional flow during a therapy with increased airway pressure, where one nare may be sealed or may be used for inspiration from the apparatus without entrainment of room air and the other nare may be used for expiration (FIGS. 4b and 4c). In a different embodiment one of the nares may be left unobstructed, providing a more comfortable therapy that has lower noise than conventional NHF therapies.

Asymmetrical flow may occur due to a pillow, cushion, divided mask or any other sealed nasal interface (FIGS. 4b and 4c). One nare may be connected to the inspiratory limb of a two-limbed ventilator circuit or to a breathing tube in a one-limbed circuit, such as a CPAP blower. The other nare may be left open (FIG. 4l), connected to conventional ventilation holes in the interface for biased flow, or connected to the expiratory limb in a two-limbed circuit ventilator. Connection to the expiratory limb of a ventilator may allow the use of flow variations to control the breathing in periodic breathing or Central Sleep Apnoea due to carbon dioxide clearance in the upper airway or re-breathing from the expiratory limb.

Opening the mouth may decrease the pressure delivered to patient and may improve clearance of anatomical dead space. A mouthpiece may be inserted to maintain the leak, and may be further connected to a negative pressure line or the expiratory limb to increase or control clearance of dead space.

To achieve comfortable asymmetrical flow, a high level of humidity, such as that delivered by the devices know as AIRVO™ or ICON™ (AIRVO™ is a humidifier with integrated flow generator device and ICON™ is a CPAP device, manufactured by Fisher & Paykel Healthcare Ltd.), may be necessary to prevent drying of the nasal epithelium. The comfort level of temperature and dew point may be determined from a ratio, and may be, but is not limited to, a range of 33° C.-37° C. and may depend on the flow rate.

Different embodiments disclose a system that allows better fitting of a nasal interface into the nares of a patient. More specifically, fittings such as, but not limited to sleeves (FIGS. 5a-5c, 5e-5f) and inserts (FIG. 5d), can be added to the nasal delivery elements of a nasal interface to optimise NHF therapy. Sleeves as described herein refer to any structure added externally to a nasal delivery element of a nasal interface. Inserts as described herein refer to any structure added internally into a nasal delivery element of a nasal interface.

Figure 7:
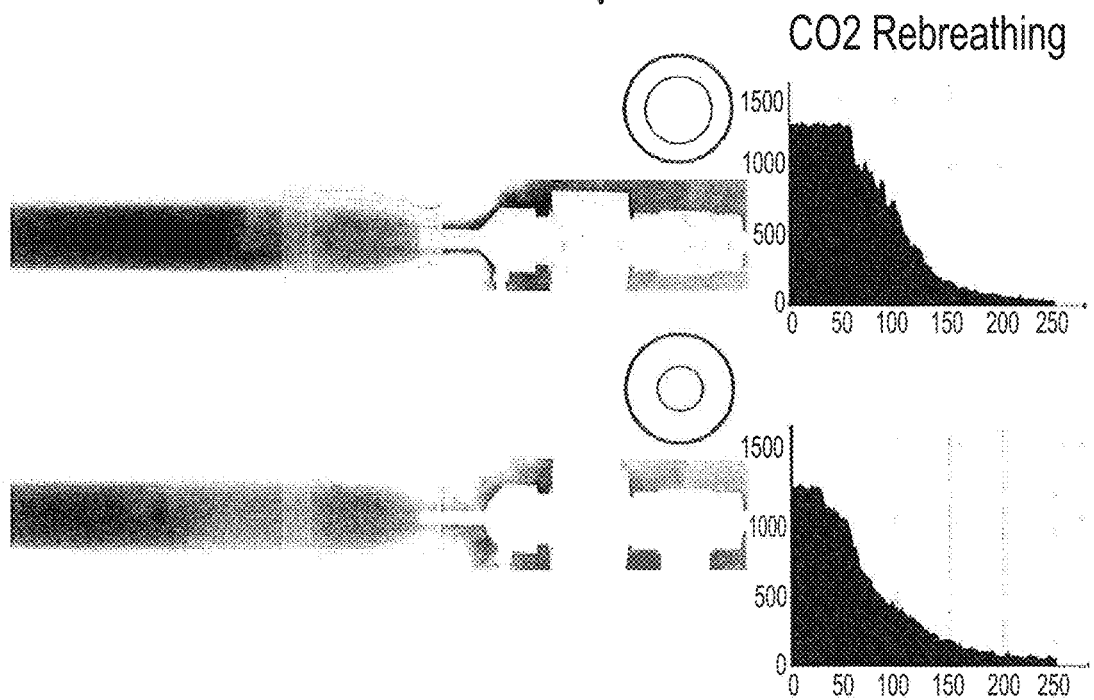
FIG. 7 depicts carbon dioxide rebreathing for nasal delivery elements of nasal interfaces with different inner diameters.
Figure 8:
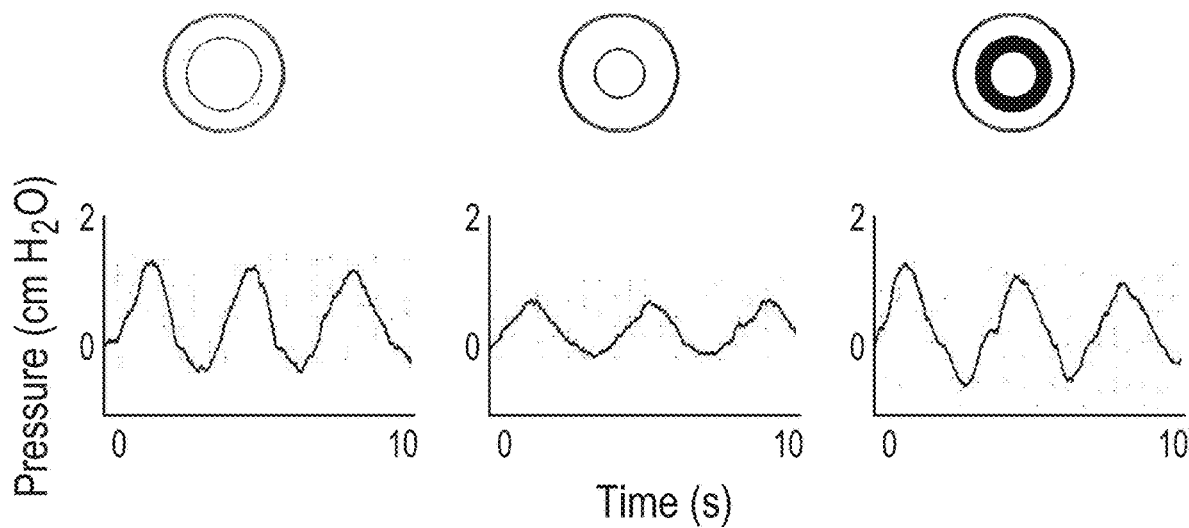
FIG. 8 depicts pressure effects for elements of nasal interfaces with different outer diameters.

The NHF therapy can be improved or optimised to deliver a desired pressure profile and efficiently clear anatomical dead space. A nasal delivery element of a nasal interface with a smaller diameter may produce a jet with a higher velocity that may more efficiently clear patient dead space than a nasal delivery element with a larger diameter. Efficient clearance of dead space reduces the amount of carbon dioxide rebreathing that occurs (FIG. 7). However a larger diameter may reduce the leak that occurs around the nasal delivery elements of the nasal interface and may result in a higher delivered pressure during both inspiration and expiration (FIG. 8). A larger diameter may be more preferable in an acute setting, particularly when a patient is suffering from respiratory distress, as a higher expiratory pressure may decrease respiratory rate and improve ventilation.

By adding fittings to the nasal delivery elements of the nasal interface, it is possible to have nasal delivery elements which combine a smaller inner and a larger outer diameter to improve or optimise dead space clearance while maintaining a high pressure at the same flow. FIG. 8 shows that a combination of a nasal delivery element with a large outer diameter and a smaller inner diameter may have similar pressure effects to a nasal delivery element with a large diameter and no insert, while a smaller inner diameter may provide less pressure. If the outer diameter is too large for a patient, the inspiratory pressure may become negative as the flow from may be lower than the peak inspiratory flow.

It generally is not desirable to increase the wall thickness of a nasal delivery element as it may be stiff in the nose of the patient, which may damage the inner surface of the nares, causing patient discomfort. However by attaching the different fittings to the interface it may be possible to benefit from the combination of the inner and outer diameters, while still providing the patient with soft nasal delivery elements to be fitted into the nares, maintaining patient comfort.

For example, by adding a sleeve onto a nasal delivery element of a nasal interface (FIGS. 5a-5b, 5e-5f), the inner diameter of the nasal delivery element remains the same and may allow jetting effects to efficiently clear the anatomical dead space, while the outer diameter has been increased to reduce the leak around the nasal delivery element and may produce higher pressure swings during breathing. The added sleeve may then be removed once the desired therapy has been delivered, or a higher pressure is no longer required. A sleeve may also function as a one-way valve which may inflate on expiration and increase expiratory pressure. To inhibit or prevent condensate accumulation a semi-permeable material may be used, a leak may be introduced, or a combination of these may be used. A sleeve may also be added to the interface to decrease the outer diameter so that it is smaller than the inner diameter (FIG. 5c), which may increase jetting effects, deviate or split the flow from the centre of the nasal delivery element to the periphery, or may combine these.

Figure 5A:
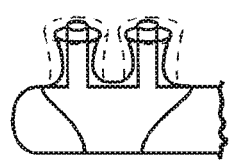
FIGS. 5a-5f are different embodiments of a nasal interface with fittings.
Figure 5B:
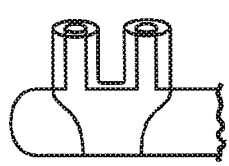
Figure 5C:
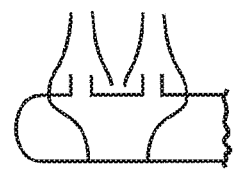
Figure 5D:
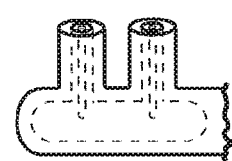
Figure 5E:
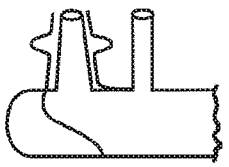

A second example is to add an insert inside the nasal delivery element (FIG. 5d). This may decrease the inner diameter to reduce pressure and increase dead space clearance, while keeping the outer diameter the same. A smaller inner diameter increases jetting effects, deviates or splits the flow from the centre of the nasal delivery element to the periphery, or may combine the flow jetting effects with deviation or splitting of the flow from the centre of the nasal delivery element to the periphery.

Figure 5F:
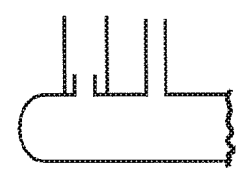

Other embodiments may include, using a fitting that may block a nasal delivery element (FIG. 5e), allowing NHF to be delivered through the unblocked nasal delivery element to the patient, using fittings that may cause asymmetrical flow to occur (FIG. 5e), or that may make an asymmetrical interface symmetrical (FIG. 5f). Adding sleeves that have been individually fit to a patient may reduce operational flow which may result in reduced noise, reduced supplemental oxygen use, improved patient comfort, and the like. Reduced operational flow may also allow less heating, water use, and the like, to be required. Only one interface is needed per patient and it can be specifically fit to the patient to vary pressure or dead space clearance.

FIG. 9 expands on embodiments described above of an asymmetrical nasal interface 100, with one nasal delivery element 200 having a greater internal cross-sectional area 205 on a plane perpendicular to the airflow direction D than the cross-sectional area 305 of other nasal delivery element 300. Referring to FIG. 9A, a nasal interface 100 comprises nasal delivery elements in the form of nasal prongs 200, 300 of substantially similar length but different internal cross-sectional areas 205, 305. Referring to FIG. 9B, a nasal interface 100 comprises nasal delivery elements in the form of nasal prong 300 and nasal pillow 200 of substantially similar length but different internal cross-sectional areas 205, 305. Referring to FIG. 9C, a nasal interface 100 comprises nasal delivery elements in the form of nasal prongs 200, 300 of different lengths and different internal cross-sectional areas 205, 305. Referring to FIGS. 9C and 9D, a nasal interface 100 comprises nasal delivery elements in the form of nasal prongs 200, 300 of different lengths and different internal cross-sectional areas 205, 305. Referring to FIG. 9E, a nasal interface 100 comprises nasal delivery elements in the form of nasal prongs 200, 300 of substantially similar length where nasal prong 300 narrows at its tip to have a smaller internal cross-sectional area 305 than cross-sectional area 205 of nasal prong 200. Referring to FIG. 9F, a nasal interface 100 comprises nasal delivery elements in the form of nasal prongs 200, 300 of substantially similar length but different internal cross-sectional areas 205, 305, where prong 200 comprises a meshed tip comprising a plurality of smaller orifices rather than a single opening. Referring to FIG. 9G, a nasal interface 100 comprises nasal delivery elements in the form of orifice 200 and nasal prong 300 of different internal cross-sectional areas 205, 305. It should be understood that in an alternative to the depicted embodiment, area 305 could be greater than area 205. Orifice 200 is formed in the rests adjacent a user's nare. Referring to FIG. 9H, a nasal interface 100 comprises nasal delivery elements in the form of nasal prongs 200, 300 carried on separate gas delivery conduits, that may or may not be held together in a single patient interface. Prongs 200, 300 are of substantially similar length but different internal cross-sectional areas 205, 305. Referring to FIG. 9I, a nasal interface 100 comprises nasal delivery elements in the form of nasal prongs 200, 300 of substantially similar length but different internal cross-sectional areas 205, 305, where the length and area of prong 200 is determined by a fitting or sleeve.

Figure 10:
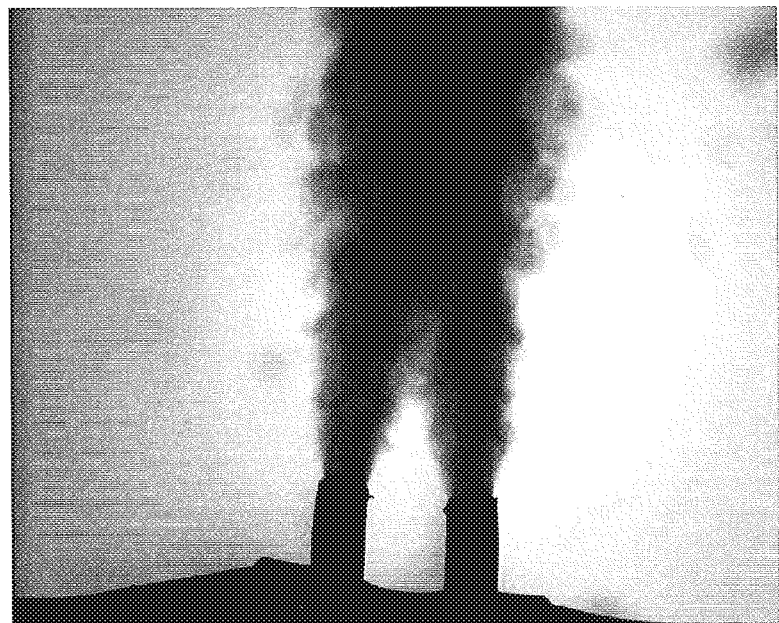
FIG. 10 is an infrared image of a symmetric carbon dioxide gas stream at a flow rate of 25 L/min.
Figure 11:
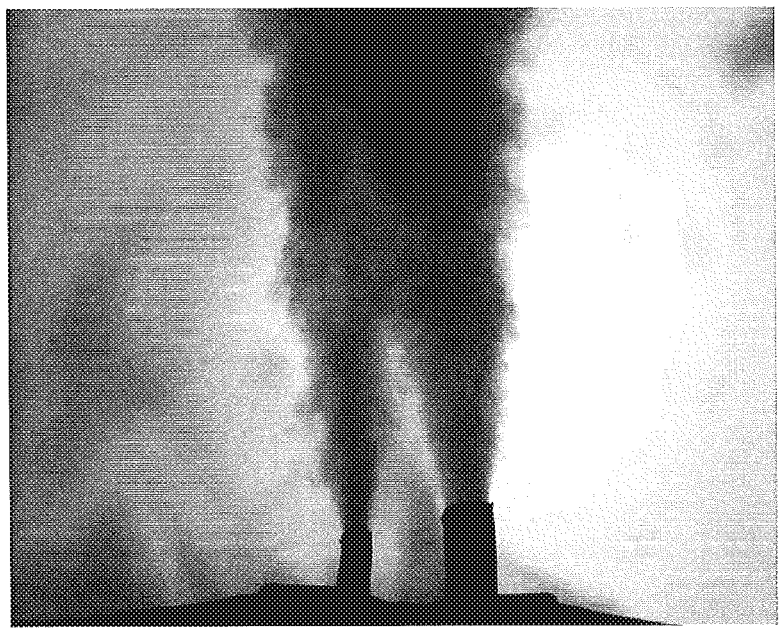
FIG. 11 is an infrared image of an asymmetric carbon dioxide gas stream at a flow rate of 25 L/min.

FIGS. 10 and 11 are infrared photographs depicting symmetric and asymmetric flows of carbon dioxide (25 L/min).

Securement System

Figure 12:
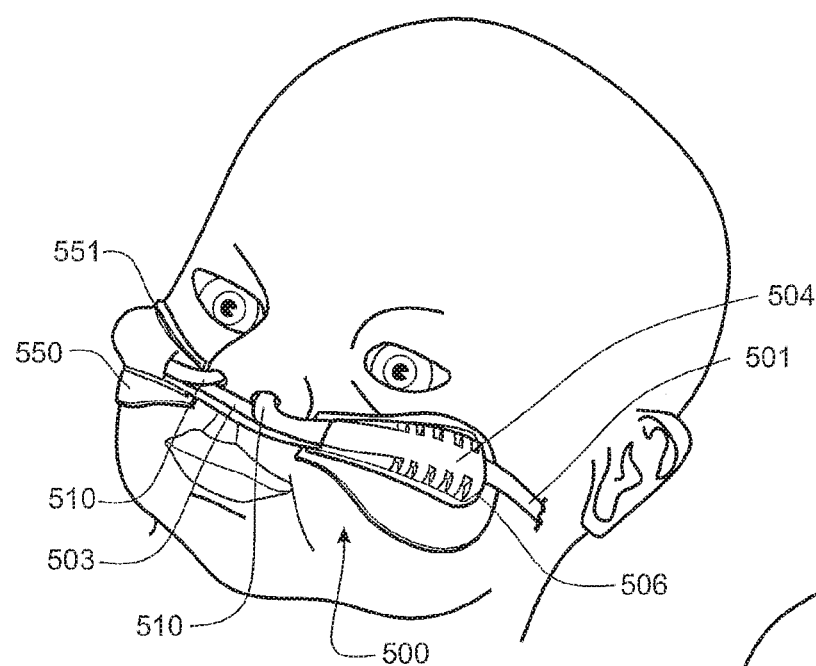
FIG. 12 shows a nasal cannula positioned in an operative position on the face of a user.
Figure 13:
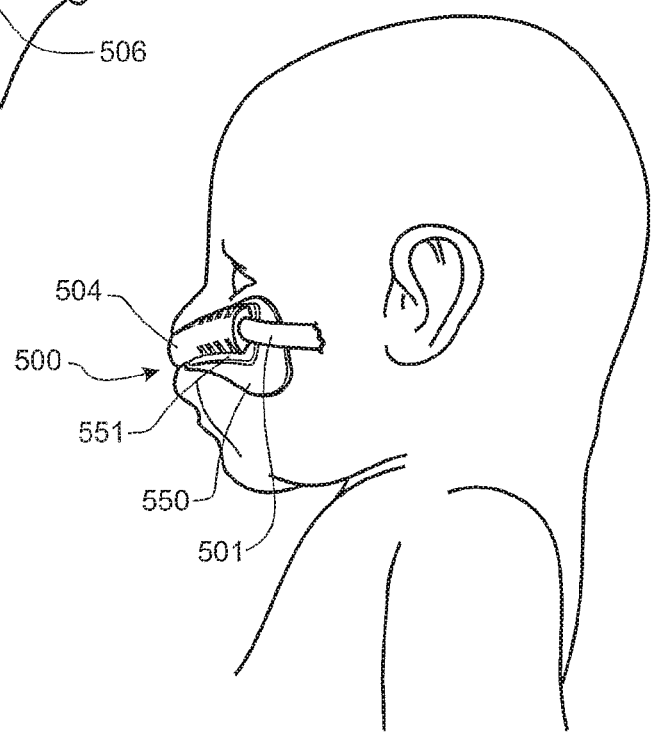
FIG. 13 is a side view of the nasal cannula arrangement of FIG. 12.
Figure 14:
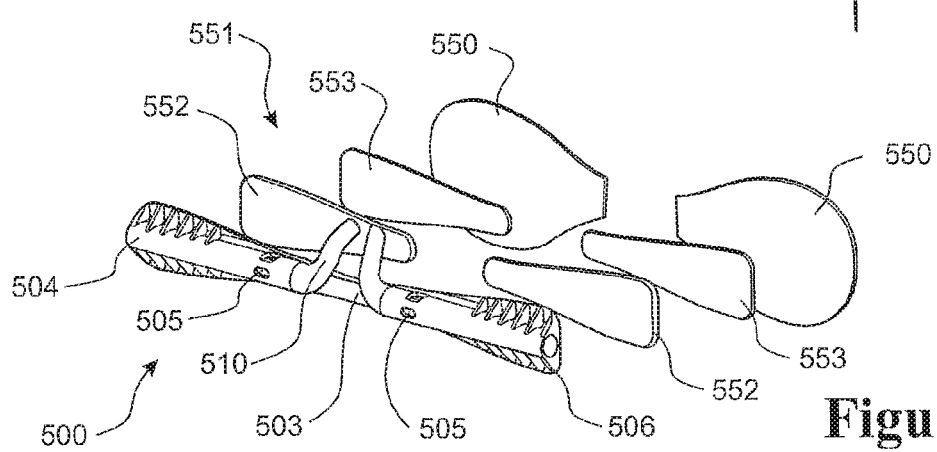
FIG. 14 shows the constituent assembly components of the embodiment of FIGS. 12 and 13.
Figure 15:
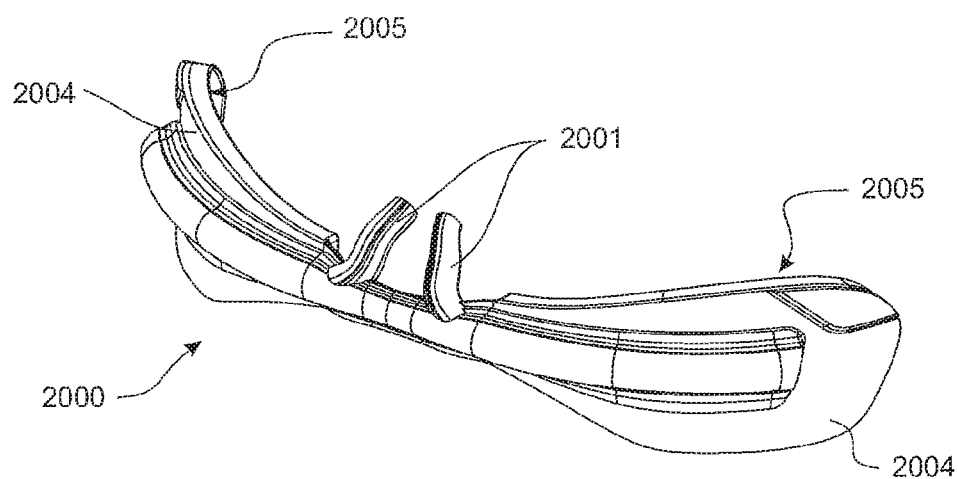
FIG. 15 is a front perspective view of a nasal cannula arrangement with a backing component comprising a lip.

A securement system for securing a user interface and/or user tubing to a patient that is useful herein is illustrated in FIGS. 12 to 14, and is described in published international application WO2012/053910, which is hereby incorporated by reference in its entirety. The securement system 500 is illustrated supporting a nasal cannula on an infant's face comprising prongs 510, a backing or harness 503 that is coupled to both prongs that retains the prongs in fixed spaced relation, and may be produced in different sizes to accommodate variations in nasal spacing. Backing 503 may also include housing 504 that generally encloses or captures at least a portion of the tube 501. The housing 504 incorporates a coupling 505 that can be used to affix headgear for retaining the interface in position. A pair of outriggers 506 project outwardly from the backing 503 on either side of the tube 501. The outriggers 506 increase a contact surface between the interface and a patient, which distributes the interface retention force over a greater area and reduces the pressure applied to a user's face. The user side face of the backing 503 and outriggers 506 (i.e., the side that rests against the face of a user) may be contoured to reflect anticipated anatomical structures. The backing 503 and the outriggers 506 also may be formed from a flexible material to allow the structure to adapt to a particular individual's face.

Beneficially, the system provides for a generally more rapid and improved or simplified ease of installation of a user interface into an operational position on a user. Further, these benefits may also contribute to improved or simplified ease of application of alternative user interfaces or removal of a user interface from a user when cycling a user between different therapies (such as gas treatments, e.g. CPAP or high-flow applications).

Certain user interfaces may be provided specifically for interaction or accommodation with the system of the described embodiments. Alternatively, nonmodified user interfaces can be accommodated by the described embodiments and can also be positioned relatively easily and with a minimum of time involved in an installation procedure.

In various embodiments provided by the securement system, such a system may provide for quick location of an interface to a user, and may provide for the secured positioning of the interface.

The ease with which a user interface may be positioned for a user is particularly useful. Providing a system whereby a carer (e.g. nurse) is able to apply the securement system with a single hand or single handedly, particularly where the interface user is an infant, is particularly advantageous.

In addition, in another embodiment, the securement system provides for a first level of securement of a user interface to a user. For example, such a first level of securement may be that as shown by FIGS. 12 to 14. Where a user requires additional or heightened security of user interface positioning or securement, a secondary level of interface securement can be utilized. Such an additional level may include application of an over patch, such as that provided, for example, by patch 660. Such a patch 660 may be an adhesive patch and can be installed over the top of the user interface and/or tubing and adhered to a portion of the dermal patch 550.

The securement system 500 comprises a two-part releasable attachment or connection arrangement 551. The releasable connection arrangement 551 acts between a pair of patches that are affixed to the patient and the user interface respectively.

The first patch is a dermal patch 550 that is adhered or otherwise attached to the patient's skin. The dermal patch has a user side that faces the user's skin and an interface side that faces the user interface. The user side of the dermal patch 550 may be attached to the skin of a user by a dermatologically sensitive adhesive, such as a hydrocolloid. The user interface side of the dermal patch is provided with the first part 553 of the two-part releasable attachment or connection system 551.

The second patch is a user interface patch 552. The user interface patch 552 also has a patient side and an interface side. The patient side of the user interface patch 552 is disposed adjacent the dermal patch when the system 500 is engaged. The complimentary second part of the two-part releasable attachment or connection system 553 is affixed to the patient side of the user interface patch 552, so that the respective parts of the two-part releasable attachment or connection system 551 are easily engageable when the patches 550, 552 are brought together. The interface side of the user interface patch 552 is affixed to the user interface. The user interface patch may be integrated with or suitably adhered to the user interface.

A part or corner of the user interface patch 552 may include a region that does not attach to the dermal patch 550. The general purpose of this is to allow a region (or tab) that can be more easily gripped by a user or carer for removing or detaching the interface from the dermal patch. For example, the backing 2004 may also comprise of such a corner region.

The two-part releasable attachment or connection arrangement 551 may comprise a hook and loop material (such as Velcro™ hook and loop material), a magnet or an array of magnets disposed on the respective patches with the poles suitably arranged, an adhesive arrangement that is activated when the patches are urged together or another suitable releasable suitable coupling. The interface side of the dermal patch 550 may have one of a hook or a loop material, and the patient side of the user interface patch 552 may have the other of the hook or loop material, such that the dermal and user interface patches are releasably attachable or connectable to each other.

When we refer to a hook and loop material, we mean any one of a wide variety of area type mechanical fasteners. For example, the Velcro™ product range includes hook and loop product where the hook component includes upstanding nylon hooks (formed as cut loops through a woven backing web) which engage with any complimentary loop pile material. The Velcro™ range also includes extruded hook products, typically of a smaller size and which mate with "fluffy" non-woven fiber backing materials. These hook materials are designed to work with a range of loop substrates and in some cases, these hook materials act as loop substrates as well. Other similar systems include the Dual-Lock™ recloseable fastener system from 3M of St Paul, Minn. USA. The common feature of these releasable fastening systems is that they engage at any part of the contact between the two parts of the system. Precise alignment of individual connectors is not required because a multitude of connectors are distributed across the area of the product. A wide range of releasable fastener systems within this field may be used in the releasable attachment system for providing releasable attachment between the dermal patch and the user interface.

The first part of the two-part releasable attachment or connection system may be adhered to the user interface side of the dermal patch with a suitable adhesive and occupy up to 100% or less than about 90%, or about 85%, or about 75%, or about 60% or about 50% or about 40% or about 30% or about 20% or about 10% of the interface side surface area of the dermal patch.

According to some embodiments, the dermal patch 550 is a generally planar pad having a thickness much less than both its width and its length. In some embodiments, the pad has an overall oval shape, but may take other shapes.

The pad includes a first part 553 of the two-part releasable attachment system 551. In some embodiments, the construction of the dermal patch is such that the first part 553 of the releasable attachment system comprises a substrate and multitude of fastener elements (with effective hooks, effective loops or other elements) provided across the area of the substrate. The substrate is secured to the body of the dermal patch. In some embodiments, the substrate is secured by adhesive or by direct bonding during forming of the dermal patch.

In some embodiments, the substrate is smaller in area than the dermal patch and is located on the dermal patch so that it does not reach any edge of the dermal patch. In this way, the edge of the substrate is spread from the edge of the dermal patch all around the perimeter of the substrate.

Nasal Cannula—First Embodiment

FIGS. 15 to 19 show a nasal cannula 2000 useful herein in detail, which is also described in published international application WO2012/053910, which is hereby incorporated by reference in its entirety. Nasal cannula arrangement 2000 comprises at least one nasal prong 2001, modified as described above, the or each prong 2001 having a gas outlet 2002 adapted to be inserted into a user's nare (or nares) and a gas inlet 2003 fluidly connected to the gas outlet 2001. The at least one nasal prong 2001 comprises a backing 2004, the backing 2004 configured to rest on a user's face, and where a lip 2005 extends about at least a part of the perimeter of a rear surface 2006 of the backing 2004. The rear surface 2004 is configured for receiving or retaining a user interface patch 2007. In use, the user interface patch 2007 may be releasably attachable or connectable to, or with, a dermal patch 2008 that is or can be affixed to a user's face.

Figure 16:
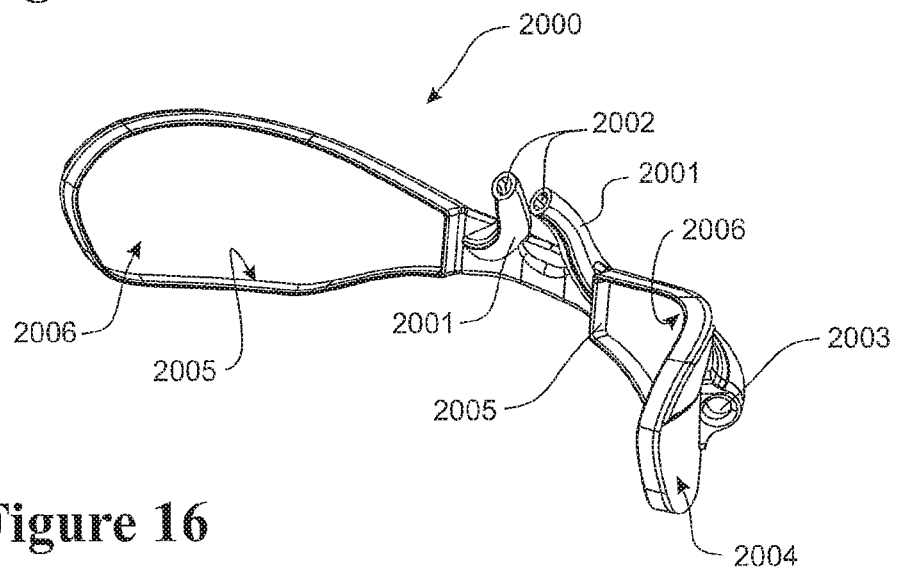
FIG. 16 is a rear perspective view of a nasal cannula arrangement with a backing component comprising a lip.
Figure 19:
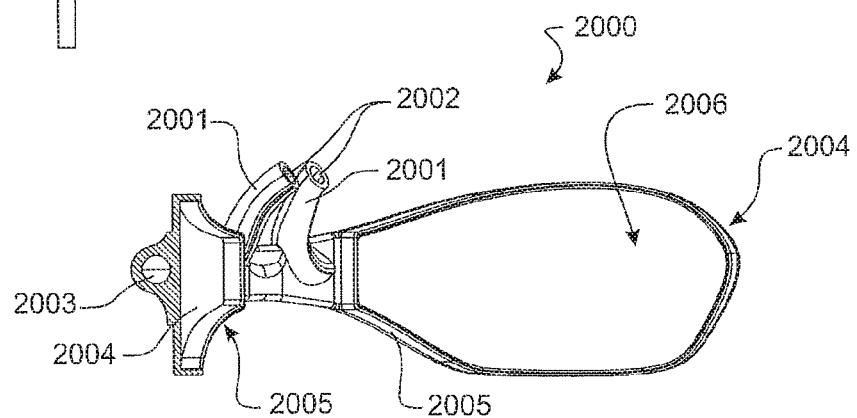
FIG. 19 is a side rear perspective view of the nasal cannula arrangement of FIGS. 15 to 18.
Figure 20:
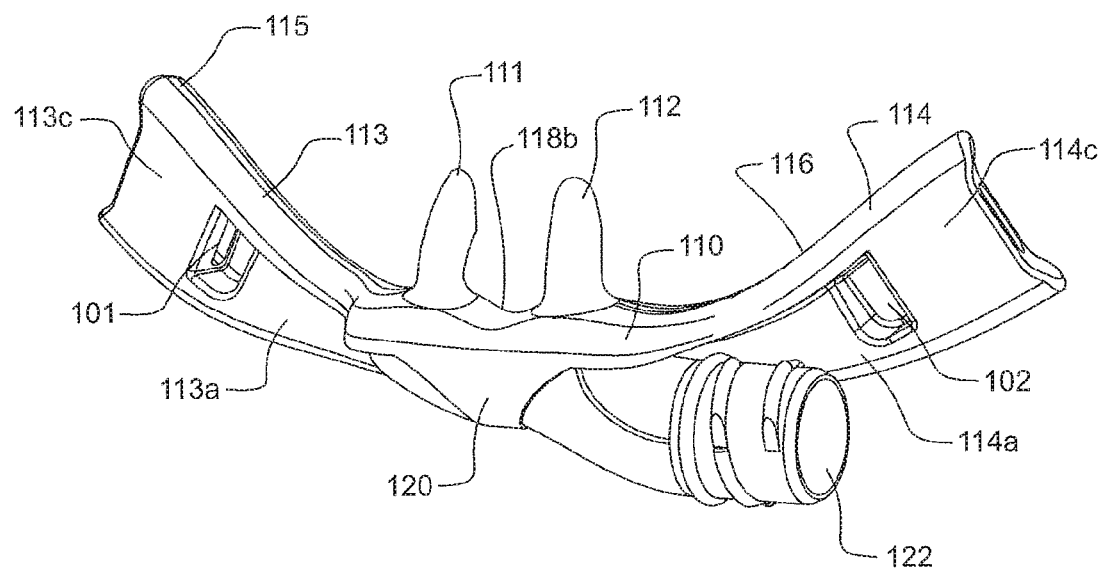
FIG. 20 is a perspective view of a face mount part of the preferred form patient interface of the invention from the outer side of the face mount part.
Figure 21:
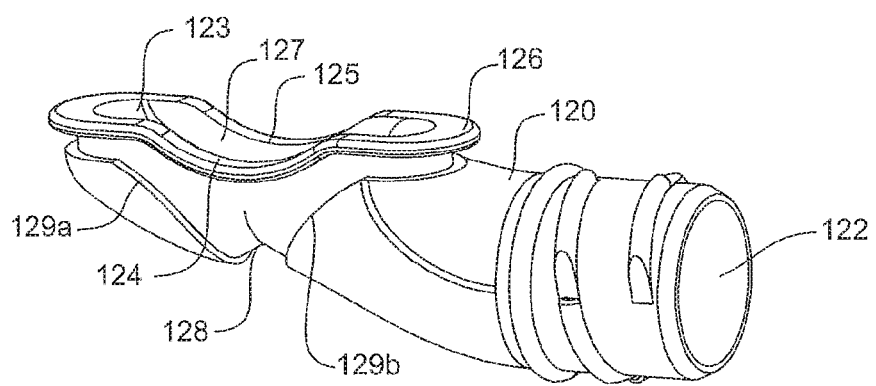
FIG. 21 is a perspective view of a gases flow manifold part of the preferred form patient interface of the invention.
Figure 22:
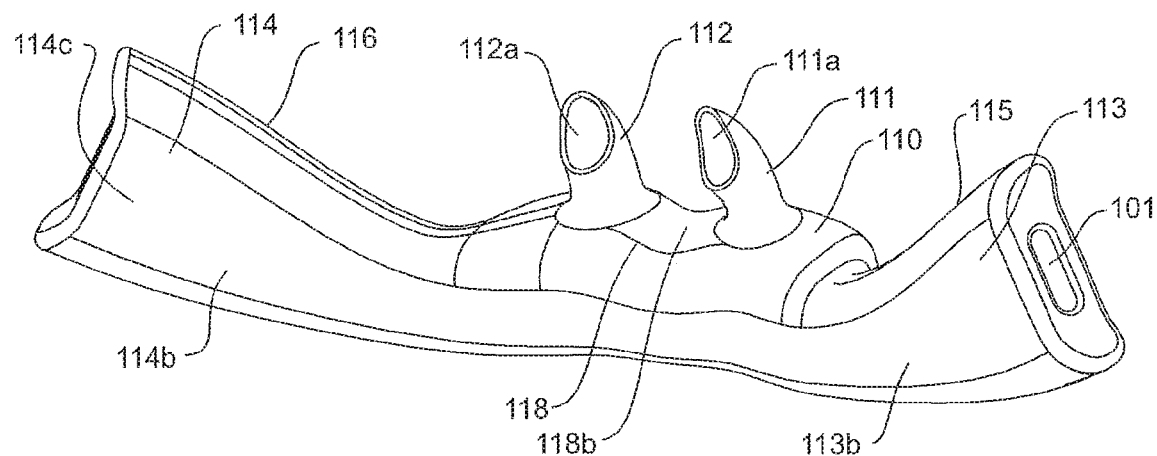
FIG. 22 is a perspective view of the face mount part of FIG. 20 from an inner side of the face mount part.
Figure 23:
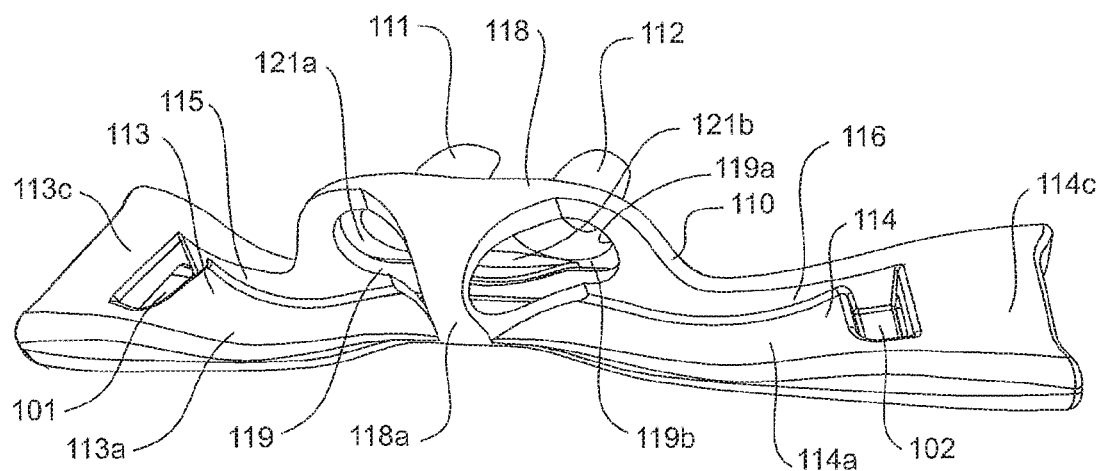
FIG. 23 is a perspective view of the face mount part of FIG. 20 from an underside of the face mount part.

As shown by FIGS. 16 and 19, the rear surface 2006 can be initially provided without a user interface patch, i.e. the surface 2006 is configured to receive or retain a user interface patch 2007. Such a user interface patch 2007 may be connected to the rear surface 2006 by an adhesive or other suitable connection. Once the patch is then in position, it is ready to be connected to or receive a dermal patch.

Figure 17:
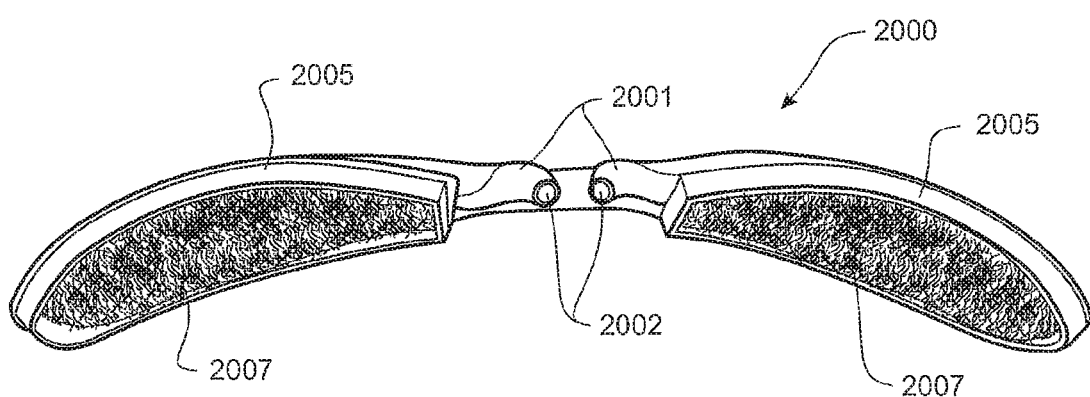
FIG. 17 is a top rear perspective view of a nasal cannula arrangement with a backing component comprising a lip and a user interface patch on a rear surface of the backing component.

In one form, the user interface patch may be one part of a two-part connection system, for example the loops of a hook and loop system. In such an instance, the interface facing surface of a dermal patch 2008 would comprise of hooks that are engageable with the loops of the user interface patch. See FIG. 17 illustrating rear surface 2006 retaining a user interface patch with loops ready for connection to the hooks of a dermal patch.

Figure 18:
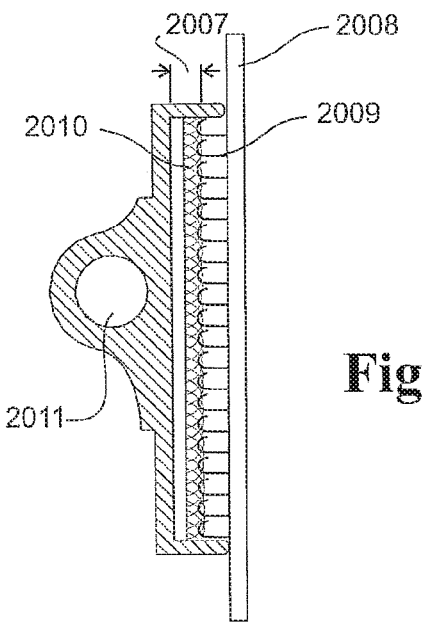
FIG. 18 is a cross sectional view through the nasal cannula arrangement of FIG. 32 when user interface patch is in connection with a dermal patch.

FIG. 18 shows a section through a cannula 2000 with the hooks 2009 of a dermal patch engaged with the loops 2010 of a user interface patch. Also shown is lumen 2011 or gas passage pathway for gas being supplied to the gas inlet of the cannula for delivery to the gas outlet 2002 of prongs 2001.

Nasal Cannula—Second Embodiment

A patient interface useful herein is shown in 20 to 23, and is described in unpublished international application PCT/NZ2014/000082, which is hereby incorporated by reference in its entirety.

Referring to FIGS. 20 to 23, the nasal prongs 111 and 112 are curved to extend into the patient's nares in use and to provide a smooth flow path for gases to flow through, and are modified to be asymmetric, as described above. The inner surfaces of the prongs 111 and 112 may be contoured to reduce noise. The bases of the prongs 111 and 112 may include curves surfaces to provide for smoother gases flow. This may reduce the noise level during operation.

In some configurations, pads may be mounted around the base of the prongs to reduce noise. The pad may be a foam material or a mouldable material that generally conforms to the patient's nose anatomy. Soft cushions or pillows may alternatively be provided.

The nasal prongs 111 and 112 are substantially hollow and substantially tubular in shape. The nasal prongs 111 and 112 may be consistent in outer diameter along their lengths but are preferably shaped to fit the contours of the nares. Each prong 111/112, where present, has an elongate opening Illa/112a at the distal end opposing a base portion 118 of the face mount part 110 to encourage a high flow of gases into the cavity. In alternative embodiments the nasal prongs 111 and 112 may have a tapered profile of a wider end at the base portion 118 and a narrower end at the openings Illa and 112a. The openings Illa and 112a may be scooped to direct the flow of gases up the patient's nares. The face mount portion 110 and in particular the nasal prongs 111 and 112 are preferably designed not to seal about the patient's nares to avoid excessive and potentially harmful build up of pressure during high flow therapy. The nasal prongs 111 and 112 are therefore sized to maintain a sufficient gap between the outer surface of the prongs 111 and 112 and the patient's skin to avoid sealing the gas path between the cannula 100 and patient. It should be understood that in the context of the present invention, the nasal prongs 111 and 112 are modified to be asymmetric, as described above.

The face mount part 110 is shaped to generally follow the contours of a patient's face around the upper lip area. The face mount part 100 is moulded or preformed to be able to conform to and/or is pliable to adapt, accommodate and/or correspond with the contours of the user's face, in the region of the face where the cannula is to be located.

The face mount part 110 comprises an elongate base portion 118 from which the nasal prongs 111 and 112 extend, and two wing portions 113 and 114 extending laterally from either side of the base portion 118. The wing portions 113 and 114 are integrally formed with the base portion 118 but may alternatively be separate parts. An inner side 119 of the base portion 118 of the face mount part 110 is formed with an elongated oval recess 119a configured to couple a corresponding outlet of the manifold 120. An arcuate bridge 118a extends from the centre of the base portion 118 to an inner wall 113a/114a of the wings to create two horizontal side entry passages 121a and 121b for insertion of the outlet 123 of the manifold 120 from either side 121a or 121b there-through.

The gases flow manifold part 120 is generally tubular in shape having a substantially annular inlet 122 at one end, and that curves around into an elongate oval outlet 123 at the opposing end. The inlet 122 is preferably removably attachable to a conduit (not shown), preferably via a threaded engagement but alternatively via a snap-fit or any other type of coupling known in the art. Alternatively, the inlet is fixedly coupled or integrally formed with a conduit. The shape of the outlet 123 corresponds with and fits into the elongate recess 119a of the face mount part 110 with a friction fit or snap fit engagement, such that substantial force, or at least a deliberate force applied by a user or a carer, is required to separate the manifold 120 from the face mount part 110.

Desirably, the inadvertent disengagement of the manifold from the face mount part is to be avoided.

An effective seal is also formed between the outlet 123 and the base portion 118 upon engagement of the two parts 110 and 120. In particular, an outer rim or lip 126 is formed about the outlet 123 which corresponds with and sealably fits into an inner groove about the periphery of the inner recess 119a to retain the outlet of the manifold 120 within the face mount part 110. Upon coupling the parts 110 and 120, the upper surface of the lip 126 engages an inner surface 119b of the base portion 118/surface 119b of the recess 119a to form an effective seal between the parts 110 and 120 for gases to flow there through. The nasal prongs 111 and 112 are aligned with corresponding apertures extending through the surface 119b of the base portion 118 to the recess 119a to fluidly connect the manifold outlet 123 with the nasal prongs 111 and 112 when coupled. The bridge 118a whilst defining the entry passages 121a and 121b for the manifold 120, also helps to retain the manifold 120 within the base 118 of the face mount part 110. A corresponding indent 128 is formed on the outer surface of the outlet 123 with opposed ridges 129a and 129b on either side to provide a push-fit engagement mechanism between the outlet 123 and the bridge 118a of the face mount part 110.

The exterior surface of the face mount portion and/or the wings 111 and 112 may comprises one or more channels to facilitate or allow air to flow between the lip and the cannula to cool the patient.

Adhesive pads may be provided on each wing 111 and 112 to facilitate coupling of the cannula 100 to the patient—especially for younger children (e.g. under 5 years old).

Each wing portion 113/114 extends laterally from the base portion 118 of the face mount part 110 and comprises an outer surface 113b/114b configured to contact against the patient's face in use, preferably at least the upper lip region of the patient's face and slightly beyond towards the user's respective cheek. The distal ends 113c and 114c of the wings 113 and 114 are configured to releasably connect respective end portions 201 and 202 of a head strap 200, described below, to retain the face mount portion 110 against the patient's face.

In a preferred embodiment, each wing 113/114 comprises an integral ridge 115/116 extending transversely along the length of the wing 113/114 from the inner side of the face mount part 110 opposing the outer surface 113b/114b of the wing 113/114. In the preferred embodiment, each ridge 115/116 is substantially perpendicular to the outer contact surface 113b/114b of the respective wing 113/114. Each ridge 115/116 preferably extends from the base portion 118 of the face mount part 110 and along an upper region of the respective wing 113/114. The ridge 115/116 acts to stabilise the face mount part 110 against the patient's face and minimise torsional stress which could otherwise cause the nasal prongs 111 and 112 to turn out and away from patient's nares. The dimensions of the ridge 115/116 including any combination of length, thickness and width (i.e. the extent to which the ridge extends away from the outer surface 113b/114b), should be sufficient to improve the stabilisation of the face mount part 110 upon the patient's face.

The ridge 115/116 may be over-moulded or integrally formed with the respective wings 113/114 of the face mount part 110.

In a preferred embodiment, the distal or terminal end 113c/114c of each wing 113/114 is accentuated or formed with a substantially greater contact surface area than a contact surface area of the wing 113/114 in the region adjacent the nasal prongs. This distal end portion 113c/114c is preferably also angled relative to a general longitudinal axis of the face mount part 110 or base 118. In particular, the distal end portion 113c/114c extends obtusely away from the base 118, or from a region of the respective wing 113/114 adjacent the base, and towards the patient's respective cheek in use. In this manner, connecting the head strap 200 to the distal end portions 113c and 114c of the wings 113 and 144 and wearing the interface 100 will create a substantially V-shaped structure that generates a force vector acting on the wings 113 and 114 and cannula 110 in the direction of the patient's cheeks. This has the effect of improving retention of the nasal prongs 111 and 112 within the patient's nares and will cause the prongs 111 and 112 to turn into the nares when the distal ends 113c and 114c of the wings 113 and 114 are pulled by the respective ends 201 and 202 of the headgear 200. Each distal end portion 113c/114c may be angled smoothly or rounded or it may be angled sharply or abruptly relative to the remainder of the respective wing 113/114.

In the preferred embodiment, the distal end portion 113c/114c is outwardly tapered to enlarge the contact surface area of the respective wing 113/114 and to also angle the distal end 113c/114c towards the patient's cheeks.

The increased surface area at the distal ends 113c and 114c provides added real estate for forming a suitable connection mechanism to couple the head strap 200. In the preferred embodiment, clip retention formations 101 and 102 are provided at each distal end 113c/114c to releasably couple clip components of the head strap 200 to the face mount portion 110 of the cannula 100.

A patient's septum and/or columella is generally quite a sensitive area and can be a source of discomfort when subjected to excessive contact pressure for prolonged periods. The present invention alleviates or reduces this pressure by providing a cushioned region of the cannula 100 adjacent the patient's septum/columella. In the preferred embodiment, the outlet 123 comprises a pair of opposed recesses or grooves 124/125 at the outer periphery for forming a dent or dip 127 in a region that locates adjacent the septum/columella in use. When coupled to the face mount portion 110, this dip 127 creates a gap between the base portion 118 and the outlet 123 of the manifold 120. In use, the gap cushions/softens the region of the cannula 100 directly adjacent the septum/columella. It disengages the pressure of the harder manifold part 120 from the septum/columella and allows the septum/columella to rest on the soft base of the face mount portion 110 only.

The base portion 118 is preferably also formed with a hollowed outer portion and/or dipped outer profile 118b between the prongs 111 and 112 to alleviate pressure at the septum/columella. The hollowing should be as much as possible without (significantly) compromising the flow delivered to the patient. The dipped portion 118b is also preferably complementary to the periphery of the outlet 123 to maintain an effective seal between the two parts of the cannula.

Headgear

Figure 24A:
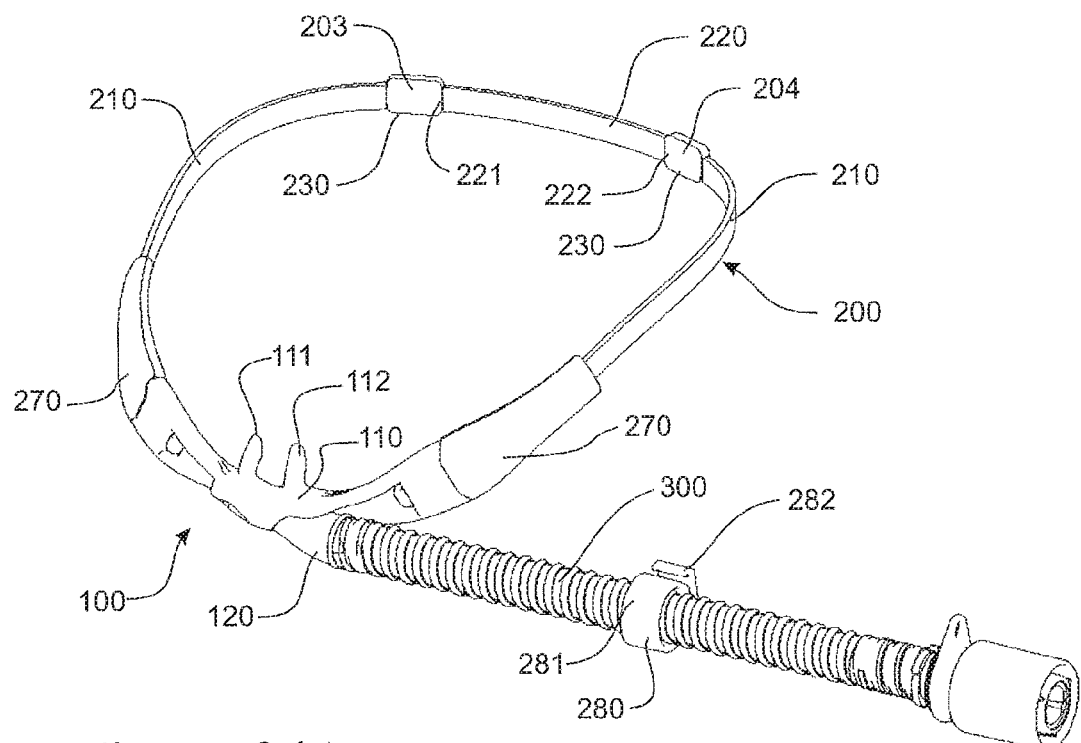
FIG. 24A is a perspective view of a preferred patient interface and headgear in an assembled state.
Figure 24B:
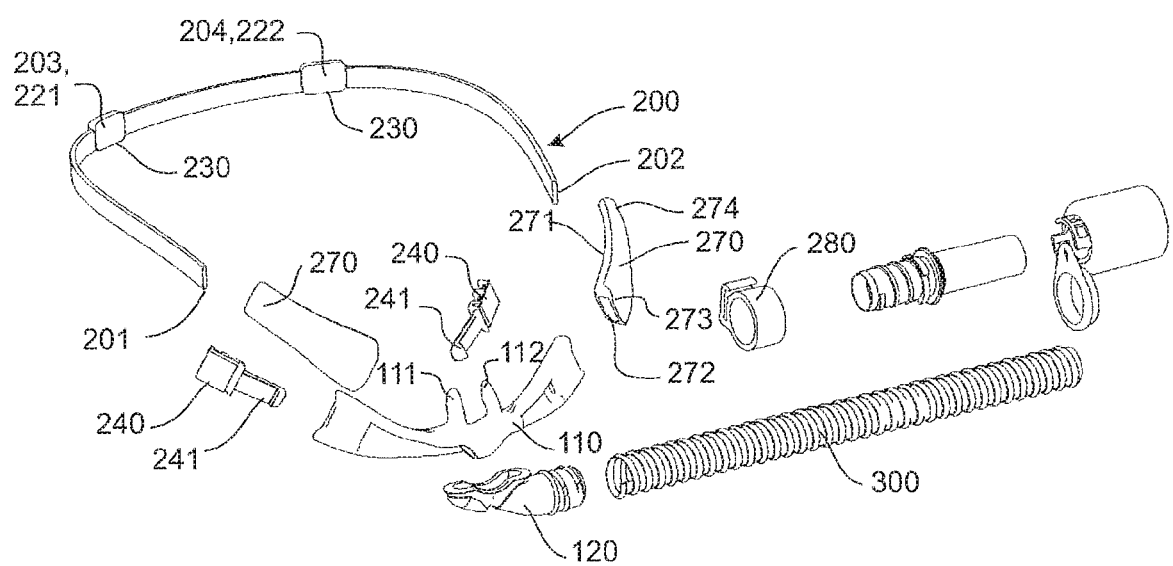
FIG. 24B is a perspective view of the patient interface and headgear of FIG. 24A in a disassembled state.

Generally, but also with reference to FIG. 24, an adjustable strap 200 the adjustment mechanism is provided in the form of one or more insertable/removable strap segments or strap extensions 220.

In an alternative embodiment, a single strap may be provided with an adjustment mechanism comprising one or more adjustment buckles, as are well known in the art, located in a central region of the strap 200 that locates adjacent the rear of the patient's head in use, or located in regions of the strap 200 that locate to the side of the patient's head, such as near end portions 201, 202.

Strap segments 220 of a fixed length can be releasably connected to the main strap 210 to extend its length. The main strap 210 in this embodiment comprises a pair of intermediate or secondary end portions 203/204 that are releasably connectable with one another, and that are also releasably connectable with respective ends 221 and 222 of the strap segments 220. When the secondary end portions 203 and 204 are connected to one another, the main strap 210 is of a continuous starting length/size for the wearer. To extend the length of the strap 200 beyond this starting length, the main strap 210 can be disconnected at the secondary end portions 203/204 and one or more additional strap segments 220 are connected there between.

A number of strap segments 220 of varying predetermined lengths may be provided to provide alternative adjustment lengths. For example, one or more strap segments 220 may be provided having a length within the range of about 1 cm to about 10 cm, or within the range of about 2 cm to about 6 cm. The strap segments 220 have lengths of, for example, about 2 cm, about 4 cm or about 6 cm. It will be appreciated that these examples are not intended to be limiting and the length of each strap segments can be of any size as it is dependent on the user and/or application.

The additional strap segments are preferably formed from a soft and stretchable/elastic material such as an elastic, textile material/fabric that are comfortable to the wearer. For example, a tubular knitted type head strap or sections of the head straps 210 may be utilised, particular for comfort over a user's ears.

It will be appreciated, particular comfort may be achieved from a head strap which is able to provide suitable locating of the patient interface in a preferred relatively stable position on a user's face, yet simultaneously provide for a relatively loose fit or low tension fit about the user's head.

Alternatively, the additional strap segments may be formed from a substantially rigid material such as a hard plastics material.

A strap connector 230 is provided at each of the secondary end portions 203/204 of the main strap 210 and the respective end portions 203/204 of the strap segments 220.

Each connector 230 is provided with a strap connection mechanism at one end to couple to the strap material, and a coupling mechanism at an opposing end to releasably couple the respective end of a similar connector 230.

In an alternative, the connector 230 may be various different forms of adjustable buckles suitable for adjusting the length or tension of the head strap sections 210 which hold the patient interface in position about a user's head.

It will also be appreciated that the connector 230 may be located so as to be off-set from a mid-point from the rear of a user's head, or may be offset to one side of a user's head. This may be advantageous so as to avoid impinging upon a part of a user's head which may otherwise be, in some positions such as sleeping, uncomfortable for the user.

In yet a further embodiment, the strap segments may be of different lengths, so as to be asymmetrically provided or to help be operational with an off-set connector 230 position. Further, it may be that of the two strap segments 210, one of those straps may be adjustable in length while the other is not. For example, one strap segment 210 may be of a permanent length or permanently connected to the connector 230.

In a preferred embodiment, the strap connection mechanism may comprise of a series of internal teeth located within the body of the connector for establishing a friction fit engagement with the respective end of the strap. A hinged jaw of the body is provided and closes upon the teeth to securely retain the end of the strap upon the teeth. The releasable coupling mechanism at the other end comprises a pair of male and female members, such as a protrusion and aperture respectively, both adapted to connect to corresponding male and female members of a similar connector 230. A lug on the protrusion may couple a recess in the female member to provide a snap-fit engagement between the members. It will be appreciated that in alternative embodiments, any other suitable connector configuration may be used to releasably connect the secondary end portions of the strap to one another, and to the end portions of the additional strap segments.

Cannula connectors 240 are provided at the primary end portions 201 and 202 of the main strap 210. These connectors 240 have a similar strap connection mechanism to the strap connectors 230 of the secondary end portions 203 and 204, but include a clip member, such as a push fit clip 241, at an end of the connector 240 opposing the strap ends, The clip 241 is configured to releasably couple the respective formation 101/102 at the side of the cannula 110. The clip member 241 is preferably a bendable part, such as a plastic part, that forms a hinged portion relative to the strap. The clip 241 is preferably preformed to have a curved shape along its length, such as one with an angle between flat and 20 degrees for example. This curve allows the clip 241 to fit the contour of the patient's face in the region of the clip 241.

Sleeve 270 may be preformed to have a curved shape along its length, such as one with an angle between flat and 20 degrees for example. The curve allows the sleeve to fit the contour of the patient's face or cheek in the region of the sleeve in use. Alternatively the sleeve 270 may take on the shape of a curved sleeve upon engagement with the primary end portion 201/202 or connector 240 of the head strap 200.

The sleeve 270 provides a surface region of relatively higher frictional surface material for frictionally engaging with the user's face or facial skin. This surface region is to be positioned for frictional engagement with the facial cheek skin of a user. The surface region is at least localised to the strap or the section of strap which is to be positioned upon the cheeks of a user. The surface region provided with the relatively higher frictional surface material is preferably of a material that is smooth and comfortable on the skin of the patient. The sleeve 270 or at least the surface region 271 is therefore formed from a relatively softer material than the connector 240.

In one preferred embodiment, the surface region 271 or the sleeve 270 is formed from a soft Thermoplastic Elastomer (TPE), but may alternatively be formed from another plastics material such as Silicone, or any other biocompatible materials.

The surface region 271 may be a surface of wider surface area more adjacent to the patient interface than the surface area more distant from the patient interface. In the preferred embodiment, the sleeve 270 tapers from a relatively wider surface area 273 to a relatively lesser surface area 274 in a direction extending away from a connection point between the connector 240 and the patient interface 100. The width of the sleeve at the end 273 is preferably the same or similar to the width of the tapered distal end 113c/114c of the corresponding wing portion 113/114 of the face mount part 110. This provides a smooth transition between the patient interface 100 and the headgear 200 for improving aesthetics and achieving a visually appealing effect.

Headgear for other forms of interface in addition to nasal cannula may comprise cheek supports 270 as described or similar, at or adjacent either side end of straps of headgear of the interface, which connect to the mask, for frictionally engaging with the user's face to stabilise the mask on the face at the cheeks, and particularly for example direct nasal masks comprising nozzles or pillows which enter or engage the nares of the wearer. Such headgear may again comprise a single head strap adapted to extend in use along the patient's cheeks, above the ears and about the back of the head, with ends comprising clips in any suitable form which couple to the mask on either side (or are permanently attached to the mask).

Patient interfaces according to the embodiments described above may be employed in a method a method of delivering gas to the airway of a subject in need thereof, improving the ventilation of a subject in need thereof, reducing the volume of anatomical dead space within the volume of the airway of a subject in need thereof, and/or treating a respiratory condition in a subject in need thereof, as described above.

Unless the context clearly requires otherwise, throughout the description and the claims, the words "comprise comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A nasal interface, comprising:
    a plurality of asymmetrical nasal delivery elements, each configured for delivery of respiratory gases to a nare of a patient comprising:
        a first nasal delivery element that is an orifice or a first nasal prong; and
        a second nasal delivery element that is a second nasal prong or a nasal pillow;
    wherein a circumference of the orifice or a first external circumference of the first nasal prong of the first nasal delivery element is different than a second external circumference of the second nasal prong or the nasal pillow of the second nasal delivery element to cause asymmetrical leak around the plurality of asymmetrical nasal delivery elements in use.

2. The nasal interface of claim 1, wherein each of the first nasal delivery element and the second nasal delivery element comprises:
    (1) the orifice adapted in use to rest adjacent one nare and the second nasal prong or the nasal pillow adapted in use to engage a second nare, or
    (2) the first nasal prong having the first external circumference and the second nasal prong or the nasal pillow having the second external circumference, the second external circumference being greater than the first external circumference, or
    (3) the first nasal prong having a first internal cross-sectional area and the second nasal prong or the nasal pillow having a second internal cross-sectional area, the second internal cross-sectional area being greater than the first internal cross-sectional area, or
    (4) the first nasal prong having the first external circumference and the first internal cross-sectional area and the second nasal prong or the nasal pillow having the second external circumference and the second internal cross-sectional area, the second external circumference and the second internal cross-sectional area being greater than the first external circumference and the first internal cross-sectional area.

3. The nasal interface of claim 1, wherein the second external circumference is between 7.5 mm and 30 mm and the first external circumference is between 20% and 80% of the second external circumference.

4. The nasal interface of claim 3, wherein the first external circumference is 50% of the second external circumference.

5. The nasal interface of claim 1, wherein a ratio of the first external circumference to the second external circumference is between 1:1.2 and 1:2.5.

6. The nasal interface of claim 5, wherein the ratio of the first external circumference to the second external circumference is 1:2.

7. The nasal interface of claim 1, the first nasal prong having a first internal cross-sectional area and the second nasal prong or the nasal pillow having a second internal cross-sectional area, wherein the second internal cross-sectional area is between 1.5 $mm^2$ and 50 $mm^2$ and the first internal cross-sectional area is between 20% and 80% of the second internal cross-sectional area.

8. The nasal interface of claim 7, wherein the first internal cross-sectional area is 50% of the second internal cross-sectional area.

9. The nasal interface of claim 1, the first nasal prong having a first internal cross-sectional area and the second nasal prong or the nasal pillow having a second internal cross-sectional area, wherein a ratio of the first internal cross-sectional area to the second internal cross-sectional area is between 1:1.2 and 1:2.5.

10. The nasal interface of claim 9, wherein the ration of the first internal cross-sectional area to the second internal cross-sectional area is 1:2.

11. The nasal interface of claim 1, wherein one or more of the plurality of asymmetrical nasal delivery elements of the nasal interface is adapted to engage with fittings to alter shape or inner or outer diameters of one or more of the plurality of asymmetrical nasal delivery elements to efficiently clear dead space, reduce operational flow, or reduce noise.

12. The nasal interface of claim 1, wherein the nasal interface is a non-sealing interface or each of the plurality of asymmetrical nasal delivery elements is sized to maintain a sufficient gap between an outer surface and a patient's nares to avoid sealing with the patient's nares.

13. The nasal interface of claim 1, wherein the second nasal delivery element causes a greater peak expiratory pressure in a patient's nares compared to the first nasal delivery element in use.

14. The nasal interface of claim 1, wherein the first external circumference and the second external circumference is a respective maximum circumference of the first nasal prong and the second nasal prong or the nasal pillow.

15. A nasal interface, comprising
    a plurality of asymmetrical nasal delivery elements, each configured for delivery of respiratory gases to a patient's nares, comprising:
        a first nasal delivery element that is an orifice or a first nasal prong; and
        a second nasal delivery element that is a second nasal prong or a nasal pillow; and
    wherein the nasal interface is a non-sealing interface or each of the plurality of asymmetrical nasal delivery elements is sized to maintain a sufficient gap between an outer surface and the patient's nares to avoid sealing with the patient's nares.

16. The nasal interface of claim 15, wherein each of the first nasal delivery element and the second nasal delivery element comprises:
    (1) the orifice adapted in use to rest adjacent one nare and the second nasal prong or the nasal pillow adapted in use to engage a second nare, or
    (2) the first nasal prong having a first external circumference and the second nasal prong or the nasal pillow having a second external circumference, the second external circumference being greater than the first external circumference, or (3) the first nasal prong having a first internal cross-sectional area and the second nasal prong or the nasal pillow having a second internal cross-sectional area, the second internal cross-sectional area being greater than the first internal cross-sectional area, or (4) the first nasal prong having the first external circumference and the first internal cross-sectional area and the second nasal prong or the nasal pillow having the second external circumference and the second internal cross-sectional area, the second external circumference and the second internal cross-sectional area being greater than the first external circumference and the first internal cross-sectional area.

17. The nasal interface of claim 16, wherein a ratio of the first external circumference to the second external circumference is between 1:1.2 and 1:2.5.

18. The nasal interface of claim 17, wherein the ratio of the first external circumference to the second external circumference is 1:2.

19. The nasal interface of claim 16, wherein the first external circumference and the second external circumference is a respective maximum circumference of the first nasal prong and the second nasal prong or the nasal pillow.

20. The nasal interface of claim 15, wherein the second nasal prong or the nasal pillow comprises a second external circumference between 7.5 mm and 30 mm and wherein the first nasal prong comprises a first external circumference being between 20% and 80% of the second external circumference.

21. The nasal interface of claim 20, wherein the first external circumference is 50% of the second external circumference.

22. The nasal interface of claim 15, the first nasal prong having a first internal cross-sectional area and the second nasal prong or the nasal pillow having a second internal cross-sectional area, wherein the second internal cross-sectional area is between 1.5 mm$^2$ and 50 mm$^2$ and the first internal cross-sectional area is between 20% and 80% of the second internal cross-sectional area.

23. The nasal interface of claim 22, wherein the first internal cross-sectional area is 50% of the second internal cross-sectional area.

24. The nasal interface of claim 22, the first nasal prong having a first internal cross-sectional area and the second nasal prong or the nasal pillow having a second internal cross-sectional area, wherein a ratio of the first internal cross-sectional area to the second internal cross-sectional area is between 1:1.2 and 1:2.5.

25. The nasal interface of claim 24, wherein the ratio of the first internal cross-sectional area to the second internal cross-sectional area is 1:2.

26. The nasal interface of claim 22, wherein one or more of the plurality of asymmetrical nasal delivery elements of the nasal interface is adapted to engage with fittings to alter a shape or inner or outer diameters of one or more of the plurality of asymmetrical nasal delivery elements to efficiently clear dead space, reduce operational flow, or reduce noise.

27. The nasal interface of claim 22, wherein the second nasal delivery element causes a greater peak expiratory pressure in the patient's nares compared to the first nasal delivery element in use.

28. A nasal interface, comprising
 a plurality of asymmetrical nasal delivery elements, each configured for delivery of respiratory gases to a patient's nares, comprising:
  a first nasal delivery element that is an orifice or a first nasal prong; and
  a second nasal delivery element that is a second nasal prong or a nasal pillow;
 wherein the first nasal delivery element and the second nasal delivery element are sized to maintain a sufficient gap between an outer surface of the first nasal delivery element and an outer surface of the second nasal delivery element and the patient's nares to avoid sealing a gas path.

* * * * *

UNITED STATES PATENT AND TRADEMARK OFFICE
CERTIFICATE OF CORRECTION

PATENT NO. : 11,565,067 B2
APPLICATION NO. : 16/798005
DATED : January 31, 2023
INVENTOR(S) : Stanislav Tatkov It is certified that error appears in the above-identified patent and that said Letters Patent is hereby corrected as shown below:

In the Specification

Column 2, Line 9, delete "airways," and insert -- airways. --.

Column 3, Line 6, after "41.5," insert -- 42, --.

Column 3, Line 12, delete "311" and insert -- 31, --.

Column 3, Line 15, after "or" insert -- 80% --.

Column 3, Line 46, delete "501 51," and insert -- 50, 51, --.

Column 3, Line 46-47, delete "641 65," and insert -- 64, 65, --.

Column 3, Line 50, delete "50/about" and insert -- 50, about --.

Column 3, Line 59-61, delete "least about 1:1.2, 1:1.25, 1:1.3, 1:1.35, 1:1.4, 1:1.45, 1:1.55, 1:1.65, 1:1.7, 1:1.75, 1:1.8, 1:1.9, 1:1.95, 1:2, 1:2.05, 1:2.1, 1:2.15, 1:2.2, 1:2.25, 1:2.3, 1:2.35, 1:2.45, or 1:2.5, and" and insert -- least about 1:1.2, 1:1.25, 1:1.3, 1:1.35, 1:1.4, 1:1.45, 1:1.5, 1:1.55, 1:1.6, 1:1.65, 1:1.7, 1:1.75, 1:1.8. 1:1.85, 1:1.9, 1:1.95, 1:2, 1:2.05, 1:2.1, 1:2.15, 1:2.2, 1:2.25, 1:2.3, 1:2.35, 1:2.4, 1:2.45, or 1:2.5, and --.

Column 5, Line 62, delete "the or" and insert -- or --.

Column 8, Line 42, delete "9A-91" and insert -- 9A-9I --.

Column 9, Line 66, delete "airways," and insert -- airways. --.

Column 12, Line 3, delete "(FIG. 41)," and insert -- (FIG. 4l), --.

Signed and Sealed this
Twenty-second Day of August, 2023

Katherine Kelly Vidal
*Director of the United States Patent and Trademark Office*

CERTIFICATE OF CORRECTION (continued)
U.S. Pat. No. 11,565,067 B2

Column 12, Line 18, delete "know" and insert -- known --.

Figure 9A:
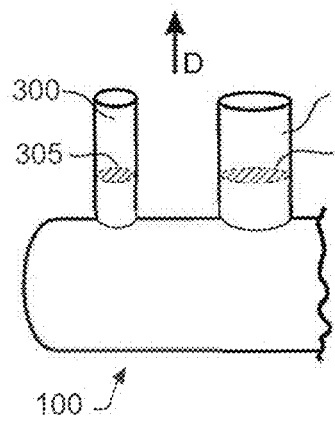
Figure 9B:
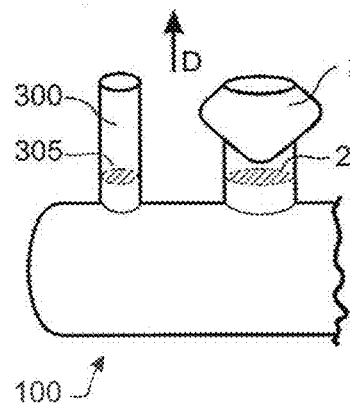
Figure 9C:
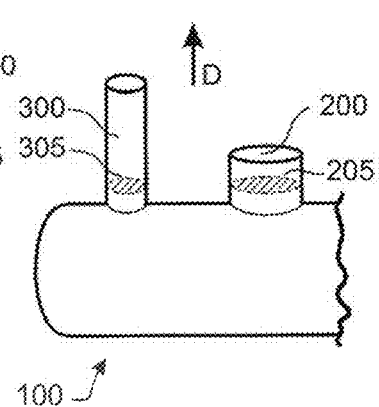
Figure 9D:
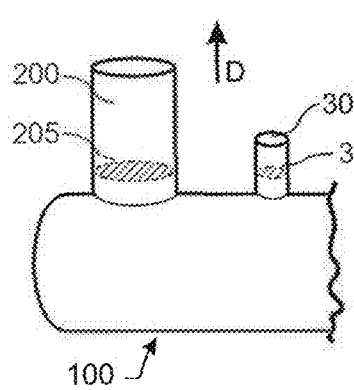
Figure 9E:
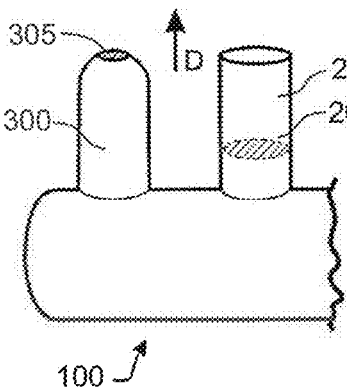
Figure 9F:
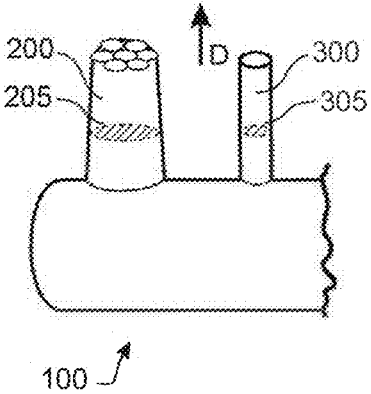
Figure 9G:
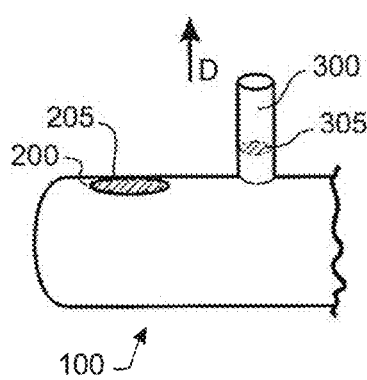
Figure 9H:
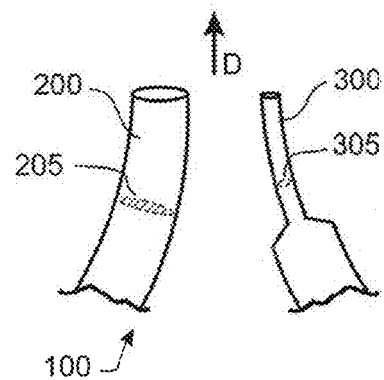
Figure 9I:
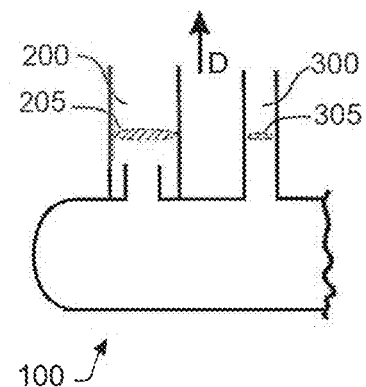

Column 14, Line 19, delete "FIG. 91," and insert -- FIG. 9I, --.

Column 16, Line 57, delete "the or" and insert -- the --.

Column 17, Line 47, delete "Illa/" and insert -- 111a/ --.

Column 17, Line 51, delete "Illa" and insert -- 111a --.

Column 17, Line 52, delete "Illa" and insert -- 111a --.

Column 21, Line 52, delete "ends," and insert -- ends. --.

Column 22, Line 60, delete "that that" and insert -- that --.

In the Claims

Column 24, Line 21, In Claim 10, delete "ration" and insert -- ratio --.